(12) United States Patent
Cheung et al.

(10) Patent No.: US 9,404,088 B2
(45) Date of Patent: Aug. 2, 2016

(54) CHITOSAN-BASED NON-VIRAL METHODS FOR TRANSFECTING GUT CELLS IN VIVO

(75) Inventors: Anthony T. Cheung, Vancouver (CA); Eric C. Hsu, Vancouver (CA)

(73) Assignee: ENGENE, INC., Montreal (CA)

( * ) Notice: Subject to any disclaimer, the term of this patent is extended or adjusted under 35 U.S.C. 154(b) by 736 days.

(21) Appl. No.: 13/070,988

(22) Filed: Mar. 24, 2011

(65) Prior Publication Data

US 2011/0171276 A1   Jul. 14, 2011

Related U.S. Application Data

(62) Division of application No. 11/694,852, filed on Mar. 30, 2007, now Pat. No. 8,846,102.

(60) Provisional application No. 60/790,083, filed on Apr. 7, 2006, provisional application No. 60/788,364, filed on Mar. 30, 2006.

(51) Int. Cl.
*A61K 47/36* (2006.01)
*C12N 15/15* (2006.01)
*C12N 5/071* (2010.01)
*A61K 9/51* (2006.01)
*A61K 48/00* (2006.01)

(52) U.S. Cl.
CPC .............. *C12N 5/0679* (2013.01); *A61K 9/5161* (2013.01); *A61K 47/36* (2013.01); *A61K 48/005* (2013.01); *A61K 48/0041* (2013.01); *A61K 48/0058* (2013.01)

(58) Field of Classification Search
CPC ............. A61K 48/0008; A61K 48/005; A61K 48/0025; A61K 47/4823; A61K 9/5161; A61K 2039/542; A61K 47/36; A61K 47/48923; B82Y 5/00; Y10S 977/616; Y10S 977/918; C12N 5/0679
See application file for complete search history.

(56) References Cited

FOREIGN PATENT DOCUMENTS

WO   WO 98/01160 A2   1/1998
WO   WO 2007/059605 A1   5/2007

OTHER PUBLICATIONS

Koping-Hoggard et al, J Gene Med, 2003, 5:130-141.*
Braat et al, Expert Opin Biol Ther, 2003, 3:725-731.*
Marjou et al, Genesis 2004 39:186-193.*
Tiyaboonachai, Naresuan University Journal, 2003, 11:51-66.*
Buschmann (Advanced Drug Delivery Reviews (2013), pp. 1-116).*
Koping-Hoggard M, et al., Improved chitosan-mediated gene delivery based on easily dissociated chitosan polyplexes of highly defined chitosan oligomers. Gene Ther. Oct. 2004;11(19):1 441-52.
Mao et al., Chitosan-DNA nanoparticles as gene carriers: synthesis, characterization and transfection efficiency. J Control Release. Feb. 23, 2001;70(3):399-421.

* cited by examiner

*Primary Examiner* — Deborah Crouch
*Assistant Examiner* — Magdalene Sgagias
(74) *Attorney, Agent, or Firm* — Arnold & Porter LLP; Todd A. Lorenz

(57) ABSTRACT

The present invention provides chitosan-based nanoparticles that can protect nucleic acids and deliver the same into gut mucosal cells. Compositions and methods for the expression of therapeutic nucleic acids in cells of the gut mucosa are provided. Compositions and methods for delivering therapeutic proteins systemically from cells of the gut mucosa are also provided.

13 Claims, 10 Drawing Sheets

CHITOSAN-BASED NON-VIRAL METHODS FOR TRANSFECTING GUT CELLS IN VIVO

CROSS-REFERENCE TO RELATED APPLICATIONS

This application is a divisional of U.S. application Ser. No. 11/694,852 (now U.S. Pat. No. 8,846,102, issued Sep. 30, 2014), filed on Mar. 30, 2007, which claims the benefit of U.S. Provisional Application No. 60/790,083, filed on Apr. 7, 2006, and U.S. Provisional Application No. 60/788,364, filed on Mar. 30, 2006. Each of the above references is incorporated herein by reference in its entirety.

FIELD

The invention relates to chitosan-based nanoparticles and nucleic acid carriers. Additionally the invention relates to methods of transfecting gut cells in vivo.

BACKGROUND

Chitosan is a non-toxic cationic copolymer of N-acetyl-D-glucosamine and D-glucosamine that possesses favorable mucosal adhesion properties and has been widely used in controlled drug delivery. The mucoadhesivity of chitosan is thought to prolong the residence time of an associated drug in the gastrointestinal tract, thereby increasing its bioavailability. (Kotze A F, Luessen H L, Thanou M, Verhoef J C, de Boer A G, Juninger H E, Lehr C M. Chitosan and chitosan derivatives as absorption enhancers for peptide drugs across mucosal epithelia. In: Mathiowitz E, Chickering D E, Lehr C M, eds. Bioadhesive Drug Delivery Systems. New York, N.Y.: Marcel Dekker; 1999.)

Several groups have explored the potential of chitosan as a DNA delivery vehicle, and the properties of a number of chitosan/DNA complexes have been examined in an attempt to identify compositions well suited for gene transfection. The complexes have been found to vary in, among other properties, solubility, propensity for aggregation, complex stability, particle size, ability to release DNA, and transfection efficiency. Chitosans of large molecular weight are relatively insoluble at physiological pH and are dissolved in acidic solution for use. Once formed, complexes containing large molecular weight chitosan and DNA are relatively stable, but poor transfection efficiencies have been reported, possibly owing to poor uptake and release of DNA. Low molecular weight chitosan/DNA complexes are more soluble but less stable in solution. Chitosan polymers of low molecular weight reportedly form unstable complexes with DNA, as indicated by separation in an electric field (agarose gel electrophoresis). Such complexes also show low transfection efficiencies and low levels of reporter gene expression in vitro (e.g., Koping-Hoggard et al., Gene Ther., 8:1108-1121, 2001; MacLaughlin, et al., J Control Release. 1998 Dec. 4; 56(1-3):259-72; Sato et al., Biomaterials, 22:2075-2080, 2001; US 2005/0170355; US 2005/0164964). Experiments have also shown that low molecular weight chitosan/DNA complexes tend to release DNA in response to challenge with salt or serum, suggesting they are poorly suited to many in vivo applications.

Studies of the effect of chitosan molecular weight on transfection efficiency in vitro have been equivocal. Some studies have shown no significant dependence on molecular weight for chitosan polymers in the size range of 20-200 kDa (Koping-Hoggard et al., supra; MacLaughlin et al, supra). However, others (Sato et al., supra) have reported that chitosans of 15 kDa and 52 kDa show higher reporter gene expression in vitro than chitosan polymers>100 kDa and chitosan polymers of 1.3 kDa are ineffective. Moreover, discordance between in vitro and in vivo transfection efficiencies has been frequently reported (e.g., Koping-Hoggard et al., Gene Ther. 2004 October; 11(19):1441-52; US 2005/0170355; US 2005/0164964).

A number of studies have examined the ability of large molecular weight chitosan/DNA complexes to transduce cells of the gastrointestinal tract. Chitosan/DNA complexes incorporating an endosomolytic peptide have been administered directly to the upper small intestine and colon have been shown to produce reporter gene expression in epithelial cells, Peyer's patches and mesenteric lymph nodes (MacLaughlin et al., supra). Additionally, oral administration of a chitosan complex with DNA encoding erythropoietin has been shown to produce a transient hematocrit increase (Chen et al., World J. Gastroenter., 10:112-116, 2004). Chitosan has also been used in a food allergy model to orally deliver DNA encoding a peanut allergen protein, Arah2, in an attempt to render mice tolerant to the ingestion of peanut extract (Roy et al., Nat. Med., 5:387-391, 1999). In all, relatively low transfection efficiencies and low levels of transgene expression have been reported, due in part to poor DNA uptake and release, but also due in part to rapid turnover of cells in the gut. The gut epithelium is one of the most rapidly renewing tissues in the body, with epithelial cell turnover every 3-5 days. Importantly, transgene expression in mucosal cells of the gut is additionally complicated by the fact that luminal mucosal cells are short-lived, providing a brief period of time for expression of DNA once it has entered the nucleus of a cell.

Other research groups have chemically modified chitosan in a variety of ways in efforts to develop DNA complexes with improved transfection efficiencies and other desirable properties, such as the ability to transduce distal gut tissue. Kai et al. point out in their report that chitosan/DNA compositions that have left the stomach and entered the more neutral environment of the duodenum lose positive charge with the attendant shift in pH, and consequently tend to release associated DNA. Kai et al. report that N-acetylation of lyophilized large molecular weight chitosan/DNA complexes stabilizes orally delivered complexes and increases efficiency of distal gut transduction. Kai et al., Pharm. Res. 21:838-843, 2004.

Given the lifespan of luminal gut mucosal cells, it is perhaps not surprising that long-term expression of genes delivered to gut mucosa by chitosan has not been reported. Additionally, the ability of chitosan DNA complexes to transfect less prevalent cell types of the gut mucosa, such as endocrine cells, has not been examined in detail. The difficulty associated with achieving long-term expression and transfection of gut endocrine cells may be appreciated by a consideration of gut structure.

The wall of the gastrointestinal canal is composed of four layers. The innermost layer of the canal is the mucosal layer, which is composed of a lining epithelium that borders the lumen. The epithelium is the site at which the body interacts with ingested materials. In areas of the gastrointestinal canal where absorption is effected, the epithelium is a single cell in thickness. The epithelium rests on a basal lamina, which in turn overlies the lamina propria. Beds of blood capillaries are densely packed in the length of lamina propria underlying absorptive regions of the canal, and it is into these vessels that the processed products of absorbed food matter pass.

The human small intestine consists of three portions: duodenum, jejunum, and ileum. The mucosa of the small intestine is extensively folded giving it a ruffled appearance as circular folds project into the intestinal lumen. Such folding fills a substantial area of the intestinal canal and increases the absorptive surface area of the epithelium by several fold. At the luminal surface, the folds of the intestinal mucosa present villi, which are evaginations of the mucosa that further increase absorptive area. Each villus, in turn, is covered by an epithelium one cell thick. This epithelium is overwhelmingly populated by absorptive enterocytes, which display thousands of short microvilli on their apical (luminal) surface, increasing the absorptive area many fold again. The outer surface of the microvilli, referred to as the glycocalyx, is filamentous and rich in carbohydrates. This membrane region is also rich in a wide variety of enzymes and transport systems facilitating the breakdown and uptake of ingested material.

Absorptive enterocytes constitute greater than 90% of the epithelial cells of the villus, and an even greater proportion of the luminal surface area. Scattered among these cells are the relatively small number of enteroendocrine cells, which reportedly constitute approximately 0.3% of the villus epithelium. In contrast to absorptive enterocytes, which present a large and ultrastructurally complex apical surface, endocrine cells have broad basal surfaces juxtaposed to capillaries of the lamina propria and narrow superiorly toward the lumen.

Even more elusive than the endocrine cells of the gut mucosa are the gut mucosal precursor cells. Inferior to the projecting villi, in the epithelium lining the depth of the crypts, lie precursor cells that give rise to the major cell types of the mucosa, including absorptive enterocytes and gut endocrine cells. The villus epithelial layer forms a continuous sheet of short-lived differentiated epithelial cells that is renewed about every three days, and maintenance of the epithelium requires an enormous amount of cell division and differentiation. Precursor cells of the crypts generate progeny that migrate out of the crypts toward villi and undergo differentiation.

Gut endocrine cells are generally characterized by their ability to secrete a synthesized protein into the blood in response to a signal or stimuli (a "secretagogue"). Particular examples of endocrine cells include K cells, L-cells, S-cells, G-cells, D-cells, I-cells, Mo-cells, Gr-cells.

K cells are located primarily in the stomach, duodenum, and jejunum. These endocrine cells secrete the hormone GIP, which normally functions to potentiate insulin release after a meal.

Gut endocrine cells generally, and K cells in particular, are attractive cellular targets for the delivery of transgenes. These cells possess the ability to process proforms of many proteins, and possess the cellular machinery that provides for regulated secretion of protein into the systemic circulation in response to cues. These properties have been exploited previously (see Cheung et al., Science, 290:1959-1962, 2000; U.S. patent application Ser. No. 09/804,409; expressly incorporated herein by reference). K cells engineered with a K-cell specific glucose-responsive insulin expression construct were observed to express and secrete insulin in response to elevated blood glucose, and were capable of restoring normal glucose tolerance in a mouse model of diabetes.

Despite a general interest in chitosan as an alternative to viral means of nucleic acid delivery, low transfection efficiency, stability and solubility problems, in vivo unpredictability, and an inability to transfect other than short-lived mucosal cells has largely prevented application of chitosan as a nucleic acid carrier in the harsh environment of the gut.

SUMMARY OF INVENTION

In one aspect, the invention provides chitosan-based nanoparticles comprising therapeutic nucleic acids that are capable of exerting a therapeutic effect when expressed in gut mucosal cells. Such chitosan-based nanoparticles provide for novel non-viral methods of treating or preventing a wide variety of conditions and disorders.

Disclosed herein are chitosan-based nanoparticles capable of producing long-term expression of therapeutic nucleic acids in gut mucosa in vivo. Such nanoparticles are useful for the long-term production of therapeutic RNAs or therapeutic proteins in gut mucosa.

Disclosed herein are chitosan-based nanoparticles capable of producing increases in the systemic levels of therapeutic proteins encoded by therapeutic nucleic acids. Such chitosan-based nanoparticles are capable of delivering physiologically relevant levels of therapeutic proteins into the blood circulatory system.

Disclosed herein are chitosan-based nanoparticles capable of transfecting gut mucosal precursor cells in vivo. Such nanoparticles are useful for the long-term production of therapeutic RNAs or therapeutic proteins in gut mucosa.

Disclosed herein are chitosan-based nanoparticles capable of transfecting gut endocrine cell precursor cells in vivo. Such nanoparticles provide for the production of therapeutic proteins in a mucosal cell type that is capable of processing proproteins and secreting therapeutic proteins in a regulated or constitutive manner into the systemic circulation.

In a number of preferred embodiments of the invention, chitosan-based nanoparticles comprise therapeutic nucleic acids encoding therapeutic proteins capable of exerting a therapeutic effect in non-gut tissue. Especially preferred are therapeutic proteins that have systemic activity.

In a number of preferred embodiments of the invention, chitosan-based nanoparticles are engineered for the non-constitutive expression of therapeutic nucleic acids in gut mucosal cells. Such nanoparticles provide for dynamic long-term expression of therapeutic nucleic acids. In a number of preferred embodiments, nanoparticles are engineered so as to provide for regulatable expression of therapeutic nucleic acids in gut mucosal cells.

In a number of preferred embodiments, nanoparticles are engineered so as to provide for the regulated secretion of therapeutic proteins from gut endocrine cells in response to a secretagogue.

In accordance with the objectives stated above, in one aspect, the invention provides compositions comprising chitosan-based nanoparticles.

In one embodiment, the invention provides a composition comprising a chitosan-based nanoparticle, which nanoparticle comprises (i) a plurality of chitosan polymers having an average molecular weight between 3 kDa and 250 kDa, and (ii) a therapeutic construct, wherein the therapeutic construct comprises a therapeutic nucleic acid operably linked to an expression control region that is functional in a gut mucosal cell, wherein the therapeutic nucleic acid is capable of exerting a therapeutic effect when expressed in the gut mucosal cell, and wherein the chitosan-based nanoparticle is capable of effecting expression of the therapeutic nucleic acid in gut mucosa for longer than about 4 days, more preferably for longer than about 5 days, more preferably for longer than about 6 days, more preferably for longer than about 7 days, more preferably for longer than about 10 days, more preferably for longer than about 2 weeks, more preferably for longer than about 3 weeks, more preferably for longer than about 4 weeks, more preferably for longer than about 6 weeks, more preferably for longer than about 8 weeks, more preferably for longer than about 10 weeks, and most preferably for longer than about 12 weeks.

In one embodiment, the invention provides a composition comprising a chitosan-based nanoparticle, which nanoparticle is capable of transfecting a gut mucosal precursor cell in vivo. Such a nanoparticle comprises (i) a plurality of chitosan polymers having an average molecular weight between 3 kDa and 250 kDa, and (ii) a therapeutic construct, wherein the therapeutic construct comprises a therapeutic nucleic acid operably linked to an expression control region that is functional in a gut mucosal cell, wherein the therapeutic nucleic acid is capable of exerting a therapeutic effect when expressed in the gut mucosal cell. In a preferred embodiment, the nanoparticle is capable of producing expression of the therapeutic nucleic acid in gut mucosa for longer than about 4 days, more preferably for longer than about 5 days, more preferably for longer than about 6 days, more preferably for longer than about 7 days, more preferably for longer than about 10 days, more preferably for longer than about 2 weeks, more preferably for longer than about 3 weeks, more preferably for longer than about 4 weeks, more preferably for longer than about 6 weeks, more preferably for longer than about 8 weeks, more preferably for longer than about 10 weeks, and most preferably for longer than about 12 weeks.

In one embodiment, the invention provides a composition comprising a chitosan-based nanoparticle, which nanoparticle is capable of increasing the systemic level of a therapeutic protein. Such a nanoparticle comprises (i) a plurality of chitosan polymers having an average molecular weight between 3 kDa and 250 kDa, and (ii) a therapeutic construct, wherein the therapeutic construct comprises a therapeutic nucleic acid operably linked to an expression control region that is functional in a gut mucosal cell, wherein the therapeutic nucleic acid is capable of exerting a therapeutic effect when expressed in the gut mucosal cell, wherein the therapeutic nucleic acid encodes a therapeutic protein that is delivered into the systemic circulation from the gut mucosa. In a preferred embodiment, the nanoparticle is capable of producing expression of the therapeutic nucleic acid in gut mucosa for longer than about 4 days, more preferably for longer than about 5 days, more preferably for longer than about 6 days, more preferably for longer than about 7 days, more preferably for longer than about 10 days, more preferably for longer than about 2 weeks, more preferably for longer than about 3 weeks, more preferably for longer than about 4 weeks, more preferably for longer than about 6 weeks, more preferably for longer than about 8 weeks, more preferably for longer than about 10 weeks, and most preferably for longer than about 12 weeks.

In one embodiment, the nanoparticle consists essentially of (i) a plurality of chitosan polymers having an average molecular weight between 3 kDa and 250 kDa, and (ii) a therapeutic construct, wherein the therapeutic construct comprises a therapeutic nucleic acid operably linked to an expression control region that is functional in a gut mucosal cell, wherein the therapeutic nucleic acid is capable of exerting a therapeutic effect when expressed in the gut mucosal cell.

In a preferred embodiment, the expression control region of a chitosan-based nanoparticle of the invention has non-constitutive activity, and the nanoparticle is capable of producing long-term dynamic expression of the therapeutic nucleic acid. In an especially preferred embodiment, the expression control region is regulatable, and the nanoparticle is capable of producing long-term regulatable expression of the therapeutic nucleic acid.

The chitosan polymers of chitosan-based nanoparticles preferably have an average molecular weight of less than about 250 kDa, more preferably less than 230 kDa, more preferably less than 220 kDa.

In another preferred embodiment, the plurality of chitosan polymers of the nanoparticle have an average molecular weight from about 3 kDa to about 210 kDa.

In another preferred embodiment, the plurality of chitosan polymers of the nanoparticle have an average molecular weight from about 10 kDa to about 250 kDa.

In another preferred embodiment, the plurality of chitosan polymers of the nanoparticle have an average molecular weight from about 10 kDa to about 210 kDa.

In another preferred embodiment, the plurality of chitosan polymers of the nanoparticle have an average molecular weight from about 3 kDa to about 50 kDa.

In another preferred embodiment, the plurality of chitosan polymers of the nanoparticle have an average molecular weight from about 3 kDa to about 6 kDa.

In another preferred embodiment, the plurality of chitosan polymers of the nanoparticle have an average molecular weight from about 200 kDa to about 210 kDa.

In a preferred embodiment, the nanoparticle has an amine:phosphate (N:P) ratio from about 1:1 to about 100:1.

In another preferred embodiment, the nanoparticle has an N:P ratio from about 1:1 to about 6:1.

In another preferred embodiment, the nanoparticle has an N:P ratio from about 1:1 to about 4:1.

In another preferred embodiment, the nanoparticle has an N:P ratio of about 3:1.

In another preferred embodiment, the nanoparticle has an N:P ratio from about 10:1 to about 90:1.

In another preferred embodiment, the nanoparticle has an N:P ratio from about 10:1 to about 50:1.

In another preferred embodiment, the nanoparticle has an N:P ratio from about 10:1 to about 40:1.

In another preferred embodiment, the nanoparticle has an N:P ratio from about 10:1 to about 30:1.

In another preferred embodiment, the nanoparticle has an N:P ratio from about 60:1 to about 100:1.

In another preferred embodiment, the nanoparticle has an N:P ratio from about 70:1 to about 100:1.

In another preferred embodiment, the nanoparticle has an N:P ratio of about 20:1.

In another preferred embodiment, the nanoparticle has an N:P ratio of about 60:1.

In a preferred embodiment, the nanoparticle has a chitosan:nucleic acid w/w ratio from about 1:1 to about 50:1.

In another preferred embodiment, the nanoparticle has a chitosan:nucleic acid w/w ratio from about 1:1 to about 5:1.

In another preferred embodiment, the nanoparticle has a chitosan:nucleic acid w/w ratio from about 1:1 to about 3:1.

In another preferred embodiment, the nanoparticle has a chitosan:nucleic acid w/w ratio of about 2:1

In another preferred embodiment, the nanoparticle has a chitosan:nucleic acid w/w ratio from about 5:1 to about 45:1.

In another preferred embodiment, the nanoparticle has a chitosan:nucleic acid w/w ratio from about 5:1 to about 25:1.

In another preferred embodiment, the nanoparticle has a chitosan:nucleic acid w/w ratio from about 5:1 to about 20:1.

In another preferred embodiment, the nanoparticle has a chitosan:nucleic acid w/w ratio from about 5:1 to about 15:1.

In another preferred embodiment, the nanoparticle has a chitosan:nucleic acid w/w ratio from about 30:1 to about 50:1.

In another preferred embodiment, the nanoparticle has a chitosan:nucleic acid w/w ratio from about 35:1 to about 50:1.

In another preferred embodiment, the nanoparticle has a chitosan:nucleic acid w/w ratio of about 10:1

In another preferred embodiment, the nanoparticle has a chitosan:nucleic acid w/w ratio of about 30:1.

In a preferred embodiment, the composition comprises nanoparticles having an average zeta potential between +5 mV and +50 mV at a pH of 5.

In another preferred embodiment, the composition comprises nanoparticles having an average zeta potential between +30 mV and +50 mV at a pH of 5.

In another preferred embodiment, the composition comprises nanoparticles having an average zeta potential between +30 mV and +40 mV at a pH of 5.

In another preferred embodiment, the composition comprises nanoparticles having an average zeta potential between +32 mV and +40 mV at a pH of 5.

In another preferred embodiment, the composition comprises nanoparticles having an average zeta potential between +5 mV and +25 mV at a pH of 5.

In another preferred embodiment, the composition comprises nanoparticles having an average zeta potential between +5 mV and +8 mV at a pH of 5.

In a preferred embodiment, the composition comprises nanoparticles having an average diameter less than 225 nm.

In another preferred embodiment, the composition comprises nanoparticles having an average diameter between 80 nm and 225 nm.

In another preferred embodiment, the composition comprises nanoparticles having an average diameter between 80 nm and 175 nm.

In a preferred embodiment, the composition has a DNA concentration of between about 1 µg/ml and about 1.5 mg/ml, more preferably between about 1 µg/ml and about 1 mg/ml, more preferably between about 10 µg/ml and about 1 mg/ml, more preferably between about 50 µg/ml and about 1 mg/ml, more preferably between about 100 µg/ml and about 1 mg/ml, more preferably between about 150 µg/ml and about 1 mg/ml, more preferably between about 200 µg/ml and about 1 mg/ml.

In a preferred embodiment, the composition has a pH of less than 6.5, more preferably less than 6.0, and most preferably between about 4.5 and about 5.5.

In a preferred embodiment, the chitosan polymers of the nanoparticle have a degree of deacetylation greater than about 70%, more preferably greater than about 75%, more preferably greater than about 80%, more preferably greater than about 85%, more preferably greater than about 90%, more preferably greater than about 95%, and most preferably at least 98%.

In a preferred embodiment, the composition comprises low molecular weight chitosan nanoparticles, wherein the plurality of chitosan polymers of the low molecular weight nanoparticles have an average molecular weight between 3 kDa and 25 kDa. In a preferred embodiment, low molecular weight chitosan nanoparticles have an N:P ratio between 10:1 and 90:1. In a preferred embodiment, low molecular weight chitosan nanoparticles have an average zeta potential between +30 mV and +50 mV, more preferably between +30 mV and +40 mV at a pH of 5. In a preferred embodiment, low molecular weight chitosan nanoparticles have an average diameter less than 175 nm.

In another embodiment, the composition comprises high molecular weight chitosan nanoparticles, wherein the plurality of chitosan polymers of the high molecular weight nanoparticles have an average molecular weight between 25 kDa and 250 kDa. In a preferred embodiment, high molecular weight chitosan nanoparticles have an N:P ratio between 2:1 and 40:1. In a preferred embodiment, high molecular weight chitosan nanoparticles have an average zeta potential between +5 mV and +25 mV at a pH of 5. In a preferred embodiment, high molecular weight chitosan nanoparticles have an average diameter less than 225 nm. In a preferred embodiment, high molecular weight chitosan nanoparticles have a chitosan:nucleic acid w/w ratio between 1:1 and 30:1.

In an especially preferred embodiment, the plurality of chitosan polymers of the nanoparticle have an average molecular weight of about 3.9 kDa, and a degree of deacetylation of about 98%. In a preferred embodiment, the composition comprises nanoparticles having an average diameter less than 175 nm. In a preferred embodiment, the composition has a DNA concentration of between about 25 µg/ml and about 100 µg/ml. In a preferred embodiment, the nanoparticle has an N:P ratio of between about 40:1 and about 80:1, most preferably an N:P ratio of about 60:1. In a preferred embodiment, the nanoparticle has a chitosan:nucleic acid w/w ratio between 20:1 and 40:1, most preferably a w/w ratio of 30:1.

In a further preferred embodiment, the plurality of chitosan polymers of the nanoparticle have an average molecular weight of about 3.9 kDa, and a degree of deacetylation of about 98%. In a preferred embodiment, the composition comprises nanoparticles having an average diameter of less than 175 nm. In a preferred embodiment, the composition has a DNA concentration of between about 200 µg/ml and about 1 mg/ml. In a preferred embodiment, the nanoparticle has an N:P ratio of between about 10:1 and about 30:1, most preferably an N:P ratio of about 20:1. In a preferred embodiment, the nanoparticle has a chitosan:nucleic acid w/w ratio between 5:1 and 15:1, most preferably a w/w ratio of 10:1.

In a preferred embodiment, a nanoparticle of the invention is capable of transfecting a gut mucosal precursor cell of the small intestine. In a preferred embodiment, the nanoparticle is capable of transfecting a gut mucosal precursor cell of the duodenum, jejunum, or ileum.

In a preferred embodiment, the nanoparticle is capable of transfecting a gut mucosal precursor cell of the stomach.

In a preferred embodiment, the nanoparticle is capable of transfecting a gut mucosal precursor cell of the colon.

In a preferred embodiment, the nanoparticle is capable of transfecting a gut endocrine cell precursor cell. In a preferred embodiment, the gut endocrine cell precursor cell is capable of producing a gut endocrine cell selected from the group consisting of K cells, L-cells, S-cells, G-cells, D-cells, I-cells, Mo-cells, and Gr-cells. In an especially preferred embodiment, the gut endocrine cell precursor cell is a K cell precursor cell.

In one embodiment, the nanoparticle lacks an endolysosomal peptide.

In one embodiment, the therapeutic nucleic acid of the nanoparticle encodes a therapeutic RNA. In a preferred embodiment, the therapeutic RNA is an siRNA, an antisense RNA, a short hairpin RNA, or an enzymatic RNA.

In a preferred embodiment, the therapeutic nucleic acid of the nanoparticle encodes a therapeutic protein. In an especially preferred embodiment, the therapeutic protein is a secreted therapeutic protein. Preferably, the nanoparticle is capable of increasing the systemic level of the secreted therapeutic protein. Preferably, the nanoparticle is capable of producing a long-term increase in the systemic level of the secreted therapeutic protein. In one embodiment, the long-term increase in the systemic level of secreted therapeutic protein is static. In a preferred embodiment, the long-term increase in the systemic level of secreted therapeutic protein is dynamic.

In a preferred embodiment, the therapeutic nucleic acid of the nanoparticle encodes a therapeutic protein that is selected from the group consisting of hormones, enzymes, cytokines, chemokines, antibodies, mitogenic factors, growth factors, differentiation factors, factors influencing angiogenesis, factors influencing blood clot formation, factors influencing blood glucose levels, factors influencing glucose metabolism, factors influencing lipid metabolism, factors influencing blood cholesterol levels, factors influencing blood LDL or HDL levels, factors influencing cell apoptosis, factors influencing food intake, factors influencing energy expenditure, factors influencing appetite, factors influencing nutrient absorption, factors influencing inflammation, and factors influencing bone formation. Particularly preferred are therapeutic nucleic acids encoding insulin, leptin, glucagon antagonist, GLP-1, GLP-2, Ghrelin, cholecystokinin, growth hormone, clotting factors, PYY, erythropoietin, inhibitors of inflammation, IL-10, IL-17 antagonists, TNFα antagonists, growth hormone releasing hormone, or parathyroid hormone. In a preferred embodiment, the encoded therapeutic protein is insulin. In another preferred embodiment, the encoded therapeutic protein is an insulin analog. In another preferred embodiment, the encoded therapeutic protein is leptin. In another preferred embodiment, the encoded therapeutic protein is PYY.

In a preferred embodiment, the therapeutic nucleic acid of the nanoparticle encodes a secreted therapeutic protein. In a preferred embodiment, the secreted therapeutic protein is capable of being secreted by regulated secretion from a gut endocrine cell. In a preferred embodiment, the secreted therapeutic protein is capable of being secreted from a gut endocrine cell in response to a secretagogue, which is preferably a nutrient. In an especially preferred embodiment, the secreted therapeutic protein is capable of being secreted from a gut endocrine cell in response to glucose.

In one embodiment, a chitosan-based nanoparticle comprises two or more distinct therapeutic nucleic acids.

In one embodiment, the expression control region of the nanoparticle does not comprise a CMV promoter.

In one embodiment, the expression control region of the nanoparticle does not comprise a viral promoter.

In a preferred embodiment, the expression control region of the nanoparticle comprises a non-constitutive promoter.

In a preferred embodiment, the expression control region of the nanoparticle comprises a gut-specific control sequence.

In a preferred embodiment, the expression control region of the nanoparticle comprises a mucosal cell-specific control sequence.

In a preferred embodiment, the expression control region of the nanoparticle comprises a gut endocrine cell-specific control sequence.

In a preferred embodiment, the expression control region of the nanoparticle comprises an inducible promoter. In one embodiment, the promoter is regulatable by a small molecule chemical compound. In another embodiment, the promoter is a nutrient-regulatable promoter. In one embodiment, the nutrient-regulatable promoter is regulated by glucose. In an especially preferred embodiment, the nutrient-regulatable promoter is a GIP promoter.

In a preferred embodiment, the therapeutic construct of the nanoparticle further comprises an integration sequence. In one embodiment, the therapeutic construct comprises a single integration sequence. In another embodiment, the therapeutic construct comprises a first and a second integration sequence, which first and second integration sequences flank the expression control region operably linked to the therapeutic nucleic acid (i.e., the expression control region and therapeutic nucleic acid taken together). In a preferred embodiment, the integration sequence(s) is functional in combination with a means for integration that is selected from the group consisting of mariner, sleeping beauty, FLP, Cre, φC31, R, lambda, and means for integration from integrating viruses such as AAV, retroviruses, and lentiviruses.

In a preferred embodiment, a chitosan-based nanoparticle further comprises a non-therapeutic construct in addition to a therapeutic construct, wherein the non-therapeutic construct comprises a nucleic acid sequence encoding a means for integration operably linked to a second expression control region that is functional in a gut mucosal precursor cell. This second expression control region and the expression control region operably linked to the therapeutic nucleic acid may be the same or different. The encoded means for integration is preferably selected from the group consisting of mariner, sleeping beauty, FLP, Cre, φC31, R, lambda, and means for integration from integrating viruses such as AAV, retroviruses, and lentiviruses.

In one embodiment, the nanoparticle consists essentially of (i) a plurality of chitosan polymers having an average molecular weight between 3 kDa and 250 kDa, (ii) a therapeutic construct, wherein the therapeutic construct comprises a therapeutic nucleic acid operably linked to an expression control region that is functional in a gut mucosal cell, wherein the therapeutic nucleic acid is capable of exerting a therapeutic effect when expressed in the gut mucosal cell, and (iii) a non-therapeutic construct, wherein said non-therapeutic construct comprises a nucleic acid sequence encoding a means for integration operably linked to a second expression control region that is functional in a gut mucosal precursor cell.

In one aspect, the invention provides a chitosan-based nanoparticle capable of transfecting a gut mucosal precursor cell in vivo, comprising (i) a plurality of chitosan polymers, and (ii) a non-therapeutic construct, wherein the non-therapeutic construct comprises a nucleic acid encoding a means for integration operably linked to an expression control region that is functional in a gut mucosal precursor cell. The encoded means for integration is preferably selected from the group consisting of mariner, sleeping beauty, FLP, Cre, φC31, R, lambda, and means for integration from integrating viruses such as AAV, retroviruses, and lentiviruses.

In one embodiment, the nanoparticle consists essentially of (i) a plurality of chitosan polymers, and (ii) a non-therapeutic construct, wherein the non-therapeutic construct comprises a nucleic acid encoding a means for integration operably linked to an expression control region that is functional in a gut mucosal precursor cell.

In one aspect, the invention provides a method for transfecting a gut mucosal cell with a therapeutic nucleic acid in vivo, comprising contacting gut mucosa in vivo with a chitosan-based nanoparticle of the invention.

In a preferred embodiment, the method involves contacting mucosa of the small intestine. In a preferred embodiment, the method involves contacting mucosa of the duodenum, jejunum, or ileum with a chitosan-based nanoparticle of the invention.

In a preferred embodiment, the method involves contacting mucosa of the stomach with a chitosan-based nanoparticle of the invention.

In a preferred embodiment, the method involves contacting mucosa of the colon with a chitosan-based nanoparticle of the invention.

In a preferred embodiment, the chitosan-based nanoparticle transfects a gut mucosal precursor cell in the gut mucosa. In a preferred embodiment, the gut mucosal precursor cell is a gut endocrine cell precursor cell. In a preferred embodiment, the gut endocrine cell precursor cell produces a gut endocrine cell selected from the group consisting of K cells, L-cells, S-cells, G-cells, D-cells, I-cells, Mo-cells, and Gr-cells. In an especially preferred embodiment, the gut endocrine cell precursor cell produces a K cell.

In a preferred embodiment, the gut mucosal precursor cell is a mucosal cell of the small intestine. In a preferred embodiment, the gut mucosal precursor cell is a mucosal cell of the duodenum, jejunum, or ileum.

In a preferred embodiment, the gut mucosal precursor cell is a mucosal cell of the stomach.

In a preferred embodiment, the gut mucosa precursor cell is a mucosal cell of the colon.

In a preferred embodiment, the gut mucosal precursor cell produces a mucosal cell that expresses the therapeutic nucleic acid.

In one embodiment, the therapeutic nucleic acid encodes a therapeutic RNA.

In a preferred embodiment, the therapeutic nucleic acid encodes a therapeutic protein. In a preferred embodiment, the therapeutic protein is a secreted therapeutic protein.

In a preferred embodiment, the therapeutic nucleic acid of the nanoparticle encodes a therapeutic protein that is selected from the group consisting of hormones, enzymes, cytokines, chemokines, antibodies, mitogenic factors, growth factors, differentiation factors, factors influencing angiogenesis, factors influencing blood clot formation, factors influencing blood glucose levels, factors influencing glucose metabolism, factors influencing lipid metabolism, factors influencing blood cholesterol levels, factors influencing blood LDL or HDL levels, factors influencing cell apoptosis, factors influencing food intake, factors influencing energy expenditure, factors influencing appetite, factors influencing nutrient absorption, factors influencing inflammation, and factors influencing bone formation. Particularly preferred are therapeutic nucleic acids encoding insulin, leptin, glucagon antagonist, GLP-1, GLP-2, Ghrelin, cholecystokinin, growth hormone, clotting factors, PYY, erythropoietin, inhibitors of inflammation, IL-10, IL-17 antagonists, TNFα antagonists, growth hormone releasing hormone, or parathyroid hormone. In a preferred embodiment, the encoded therapeutic protein is insulin. In another preferred embodiment, the encoded therapeutic protein is an insulin analog. In another preferred embodiment, the encoded therapeutic protein is leptin. In another preferred embodiment, the encoded therapeutic protein is PYY.

In a preferred embodiment, the therapeutic protein is produced in a gut mucosal cell and enters the systemic circulation such that the systemic level of the therapeutic protein is increased. In a preferred embodiment, the therapeutic protein is released by regulated secretion into the systemic circulation.

In a preferred embodiment, the systemic level of the therapeutic protein is increased for longer than about 4 days, more preferably longer than about 5 days, more preferably longer than about 6 days, more preferably longer than about 7 days, more preferably longer than about 10 days, more preferably longer than about 2 weeks, more preferably longer than about 3 weeks, more preferably longer than about 4 weeks, more preferably longer than about 6 weeks, more preferably longer than about 8 weeks, more preferably longer than about 10 weeks, and most preferably longer than about 12 weeks.

In one embodiment, the increase in the systemic level of the therapeutic protein is static. In a preferred embodiment, the increase in the systemic level of the therapeutic protein is dynamic.

In one embodiment, the method comprises contacting gut mucosa in vivo with a first chitosan-based nanoparticle and a second chitosan-based nanoparticle. The first chitosan based nanoparticle is capable of transfecting a gut mucosal precursor cell in vivo and comprises (i) a plurality of chitosan polymers, and (ii) a therapeutic construct, wherein the therapeutic construct comprises a therapeutic nucleic acid operably linked to an expression control region functional in a gut mucosal cell, and an integration sequence. The second chitosan-based nanoparticle is capable of transfecting a gut mucosal precursor cell in vivo and comprises (i) a plurality of chitosan polymers, and (ii) a non-therapeutic construct, wherein the non-therapeutic construct comprises a nucleic acid encoding a means for integration operably linked to an expression control region that is functional in a gut mucosal precursor cell. Without being bound by theory, it appears that a gut mucosal precursor cell in the gut mucosa is transfected with the first and second nanoparticles. The nucleic acid of the second nanoparticle is expressed in the gut mucosal precursor cell to produce a means for integration, whereby the means for integration integrates the therapeutic nucleic acid operably linked to an expression control region provided by the first nanoparticle into the genome of the gut mucosal precursor cell.

In another embodiment, the method comprises contacting gut mucosa in vivo with a chitosan-based nanoparticle comprising (i) a plurality of chitosan polymers; (ii) a therapeutic construct, wherein the therapeutic construct comprises a therapeutic nucleic acid operably linked to an expression control region functional in a gut mucosal cell, and an integration sequence; and (iii) a non-therapeutic construct, wherein the non-therapeutic construct comprises a nucleic acid encoding a means for integration operably linked to an expression control region that is functional in a gut mucosal precursor cell. Without being bound by theory, it appears that a gut mucosal precursor cell in the gut mucosa is transfected using the nanoparticle. The nucleic acid encoding a means for integration is expressed in the gut mucosal precursor cell to produce a means for integration, whereby the means for integration integrates the therapeutic nucleic acid operably linked to an expression control region into the genome of the gut mucosal precursor cell.

It will be appreciated that optimal ratios of therapeutic and non-therapeutic constructs for facilitating integration may vary depending upon the particular means of integration contemplated for use. Determining the optimal ratios of therapeutic to non-therapeutic constructs is done by one of reasonable skill in the art without undue experimentation.

In one aspect, the invention provides methods for effecting long-term expression of a therapeutic nucleic acid in a mammalian gut mucosal cell. The methods involve contacting the gut mucosa of a mammal with a chitosan-based nanoparticle of the invention, wherein the nanoparticle comprises a therapeutic nucleic acid, and wherein the therapeutic nucleic acid is expressed in a gut mucosal cell of the mammal.

In one embodiment, the methods comprise the use of a nanoparticle of the invention, which nanoparticle comprises a therapeutic construct and a non-therapeutic construct.

In one embodiment, the methods comprise the use of two nanoparticles of the invention, the first comprising a therapeutic construct and the second comprising a non-therapeutic construct.

In one aspect, the invention provides methods for increasing the systemic level of a secreted therapeutic protein in a mammal. The methods comprise contacting gut mucosa of a mammal with a chitosan-based nanoparticle of the invention, wherein the nanoparticle comprises a therapeutic nucleic acid encoding a secreted therapeutic protein, wherein the secreted therapeutic protein is produced in a mucosal cell of the gut mucosa, and wherein the secreted therapeutic protein produced in the mucosal cell enters the systemic circulation such that the systemic level of the secreted therapeutic protein is increased.

In one embodiment, the methods comprise the use of a nanoparticle of the invention, which nanoparticle comprises a therapeutic construct and a non-therapeutic construct.

In one embodiment, the methods comprise the use of two nanoparticles of the invention, the first comprising a therapeutic construct and the second comprising a non-therapeutic construct.

In one aspect, the invention provides methods for treating patients having diseases or conditions treatable by increasing the systemic level of a therapeutic protein. The methods comprise contacting gut mucosa of a patient with a chitosan-based nanoparticle of the invention, wherein the nanoparticle comprises a therapeutic nucleic acid encoding a secreted therapeutic protein, wherein the secreted therapeutic protein is produced in a mucosal cell of the gut mucosa of the patient, and wherein the secreted therapeutic protein produced in the mucosal cell enters the systemic circulation such that the systemic level of the secreted therapeutic protein is increased to a therapeutically effective level.

In a preferred embodiment, the disease is a metabolic disease.

In a preferred embodiment, the disease is diabetes mellitus.

In another preferred embodiment, the condition is morbid obesity.

In another preferred embodiment, the condition is growth deficiency.

In a preferred embodiment, the chitosan-based nanoparticle is orally administered.

In a preferred embodiment, the chitosan-based nanoparticle is administered endoscopically.

In a preferred embodiment, the chitosan-based nanoparticle is administered rectally.

In a preferred embodiment, the mucosal cell is a gut endocrine cell. In a preferred embodiment, the gut endocrine cell is selected from the group consisting of K cells, L-cells, S-cells, G-cells, D-cells, I-cells, Mo-cells, and Gr-cells. In an especially preferred embodiment, the gut endocrine cell is a K cell.

In a preferred embodiment, the mucosal cell is a mucosal cell of the small intestine. In a preferred embodiment, the mucosal cell is a mucosal cell of the duodenum, jejunum, or ileum.

In a preferred embodiment, the mucosal cell is a mucosal cell of the stomach.

In a preferred embodiment, the mucosal cell is a mucosal cell of the colon.

In a preferred embodiment, the therapeutic nucleic acid of the nanoparticle encodes a therapeutic protein that is selected from the group consisting of hormones, enzymes, cytokines, chemokines, antibodies, mitogenic factors, growth factors, differentiation factors, factors influencing angiogenesis, factors influencing blood clot formation, factors influencing blood glucose levels, factors influencing glucose metabolism, factors influencing lipid metabolism, factors influencing blood cholesterol levels, factors influencing blood LDL or HDL levels, factors influencing cell apoptosis, factors influencing food intake, factors influencing energy expenditure, factors influencing appetite, factors influencing nutrient absorption, factors influencing inflammation, and factors influencing bone formation. Particularly preferred are therapeutic nucleic acids encoding insulin, leptin, glucagon antagonist, GLP-1, GLP-2, Ghrelin, cholecystokinin, growth hormone, clotting factors, PYY, erythropoietin, inhibitors of inflammation, IL-10, IL-17 antagonists, TNFα antagonists, growth hormone releasing hormone, or parathyroid hormone. In a preferred embodiment, the encoded therapeutic protein is insulin. In another preferred embodiment, the encoded therapeutic protein is an insulin analog. In another preferred embodiment, the encoded therapeutic protein is leptin. In another preferred embodiment, the encoded therapeutic protein is PYY.

In a preferred embodiment, the secreted therapeutic protein is released by regulated secretion from a gut endocrine cell.

In a preferred embodiment, the systemic level of the secreted therapeutic protein is increased for longer than about 4 days, more preferably longer than about 5 days, more preferably longer than about 6 days, more preferably longer than about 7 days, more preferably longer than about 10 days, more preferably longer than about 2 weeks, more preferably longer than about 3 weeks, more preferably longer than about 4 weeks, more preferably longer than about 6 weeks, more preferably longer than about 8 weeks, more preferably longer than about 10 weeks, and most preferably longer than about 12 weeks.

In one embodiment, the methods comprise the use of a nanoparticle of the invention, which nanoparticle comprises a therapeutic construct and a non-therapeutic construct.

In one embodiment, the methods comprise the use of two nanoparticles of the invention, the first comprising a therapeutic construct and the second comprising a non-therapeutic construct.

In one aspect, the invention provides pharmaceutical compositions comprising chitosan-based nanoparticles of the invention.

In one embodiment, the invention provides pharmaceutical compositions capable of increasing the systemic level of therapeutic proteins. Such a pharmaceutical composition comprises a chitosan-based nanoparticle of the invention, wherein the nanoparticle comprises a therapeutic nucleic acid encoding a secreted therapeutic protein.

In one embodiment, the pharmaceutical composition comprises two or more distinct therapeutic nucleic acids of the invention.

In one embodiment, the pharmaceutical composition comprises a first chitosan-based nanoparticle of the invention and a second chitosan-based nanoparticle of the invention, wherein the first and second nanoparticle comprise distinct therapeutic nucleic acids.

In one embodiment, the pharmaceutical composition comprises a therapeutic construct and a non-therapeutic construct of the invention.

In one embodiment, the pharmaceutical composition comprises a first chitosan-based nanoparticle of the invention and a second chitosan-based nanoparticle of the invention, wherein the first nanoparticle comprises a therapeutic construct, and the second nanoparticle comprises a non-therapeutic construct.

In a preferred embodiment, the pharmaceutical composition is capable of increasing the systemic level of the therapeutic protein for longer than about 4 days, more preferably longer than about 5 days, more preferably longer than about 6 days, more preferably longer than about 7 days, more preferably longer than about 10 days, more preferably longer than about 2 weeks, more preferably longer than about 3 weeks, more preferably longer than about 4 weeks, more preferably longer than about 6 weeks, more preferably longer than about 8 weeks, more preferably longer than about 10 weeks, and most preferably longer than about 12 weeks.

In a preferred embodiment, the pharmaceutical composition may be administered orally.

In a preferred embodiment, the pharmaceutical composition may be administered endoscopically.

In a preferred embodiment, the pharmaceutical composition may be administered rectally.

In one aspect, the invention provides a modified gut mucosal cell, which is produced by contacting gut mucosa in vivo with a chitosan-based nanoparticle according to a method disclosed herein.

In one aspect, the invention provides methods of producing chitosan-based nanoparticles of the invention. In one embodiment, methods for producing nanoparticles capable of producing long-term expression of therapeutic nucleic acids in gut mucosal cells are provided. The methods involve the formation of a nanoparticle preparation mixture.

In a preferred embodiment, chitosan polymers having an average molecular weight from about 3 kDa to about 250 kDa are used.

In another preferred embodiment, chitosan polymers having an average molecular weight from about 3 kDa to about 210 kDa are used.

In another preferred embodiment, chitosan polymers having an average molecular weight from about 10 kDa to about 250 kDa are used.

In another preferred embodiment, chitosan polymers having an average molecular weight from about 10 kDa to about 210 kDa are used.

In another preferred embodiment, chitosan polymers having an average molecular weight from about 3 kDa to about 50 kDa are used.

In another preferred embodiment, chitosan polymers having an average molecular weight from about 3 kDa to about 6 kDa are used.

In another preferred embodiment, chitosan polymers having an average molecular weight from about 200 kDa to about 210 kDa are used.

In a preferred embodiment, the nanoparticle preparation mixture has an amine:phosphate (N:P) ratio from about 1:1 to about 100:1.

In another preferred embodiment, the nanoparticle preparation mixture has an N:P ratio from about 1:1 to about 6:1.

In another preferred embodiment, the nanoparticle preparation mixture has an N:P ratio from about 1:1 to about 4:1.

In another preferred embodiment, the nanoparticle preparation mixture has an N:P of about 3:1.

In another preferred embodiment, the nanoparticle preparation mixture has an N:P ratio from about 10:1 to about 90:1.

In another preferred embodiment, the nanoparticle preparation mixture has an N:P ratio from about 10:1 to about 50:1.

In another preferred embodiment, the nanoparticle preparation mixture has an N:P ratio from about 10:1 to about 40:1.

In another preferred embodiment, the nanoparticle preparation mixture has an N:P ratio from about 10:1 to about 30:1.

In another preferred embodiment, the nanoparticle preparation mixture has an N:P ratio from about 60:1 to about 100:1.

In another preferred embodiment, the nanoparticle preparation mixture has an N:P ratio from about 70:1 to about 100:1.

In another preferred embodiment, the nanoparticle preparation mixture has an N:P ratio of about 20:1.

In another preferred embodiment, the nanoparticle preparation mixture has an N:P ratio of about 60:1.

In a preferred embodiment, the nanoparticle preparation mixture has a chitosan:nucleic acid w/w ratio from about 1:1 to about 50:1.

In another preferred embodiment, the nanoparticle preparation mixture has a chitosan:nucleic acid w/w ratio from about 1:1 to about 5:1.

In another preferred embodiment, the nanoparticle preparation mixture has a chitosan:nucleic acid w/w ratio from about 1:1 to about 3:1.

In another preferred embodiment, the nanoparticle preparation mixture has a chitosan:nucleic acid w/w ratio of about 2:1.

In another preferred embodiment, the nanoparticle preparation mixture has a chitosan:nucleic acid w/w ratio from about 5:1 to about 45:1.

In another preferred embodiment, the nanoparticle preparation mixture has a chitosan:nucleic acid w/w ratio from about 5:1 to about 25:1.

In another preferred embodiment, the nanoparticle preparation mixture has a chitosan:nucleic acid w/w ratio from about 5:1 to about 20:1.

In another preferred embodiment, the nanoparticle preparation mixture has a chitosan:nucleic acid w/w ratio from about 5:1 to about 15:1.

In another preferred embodiment, the nanoparticle preparation mixture has a chitosan:nucleic acid w/w ratio from about 30:1 to about 50:1.

In another preferred embodiment, the nanoparticle preparation mixture has a chitosan:nucleic acid w/w ratio from about 35:1 to about 50:1.

In another preferred embodiment, the nanoparticle preparation mixture has a chitosan:nucleic acid w/w ratio of about 10:1.

In another preferred embodiment, the nanoparticle preparation mixture has a chitosan:nucleic acid w/w ratio of about 30:1.

In one aspect, the invention provides chitosan-based nanoparticles produced by a nanoparticle production method disclosed herein.

In one aspect, the invention provides a method for preparing a medicament useful for the treatment of a disease or condition that is treatable by increasing the systemic level of a secreted therapeutic protein. The methods involve methods of producing chitosan-based nanoparticles disclosed herein.

DETAILED DESCRIPTION

Gut Mucosal Cells

Figure 1:
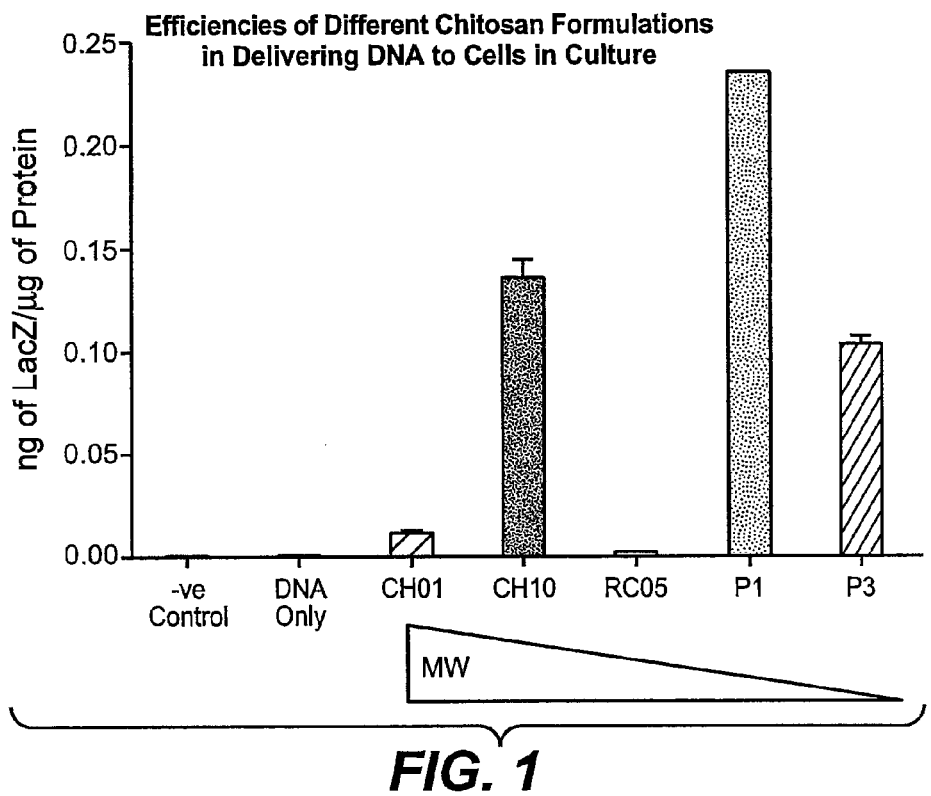
FIG. 1 shows results of in vitro transfection of 293 T cells with chitosan-based nanoparticles comprising chitosan polymers of various molecular weights, as indicated.

As used herein, "gut mucosal cell" refers to a cell of the gut mucosa. Included among gut mucosal cells are endocrine cells, non-endocrine cells, and precursors thereof. Gut mucosal precursor cells include stem cells. A gut mucosal precursor cell is directly or indirectly a precursor of a differentiated cell type of the gut mucosa. Gut mucosal precursor cells include undifferentiated gut mucosal cells. Gut mucosal precursor cells give rise to major cell types of the gut mucosa, including endocrine cells and non-endocrine cells. A gut endocrine cell precursor cell is a precursor of a gut mucosal cell that is a gut endocrine cell, e.g., a K cell.

Particular examples of gut mucosal cells include endocrine cells, such as K cells, L-cells, S-cells, G-cells, D-cells, I-cells, Mo-cells, Gr-cells, and non-endocrine cells such as absorptive enterocytes. Endocrine cells are generally characterized by their ability to secrete a synthesized protein into the blood in response to a signal or stimuli (a "secretagogue"). Non-endocrine cells are generally not known to secrete a synthesized protein into the blood in response to a signal or stimuli.

Especially preferred gut endocrine cells for use in the invention are K cells (Sandstrom O., El-Salhy M., Mech. Ageing Dev. 108:39 (1999)).

A partial list of several types of gut endocrine cells and proteins normally produced thereby are shown in Table 1.

TABLE 1

| Cell Type | Peptide |
| --- | --- |
| G-cells | Gastrin |
| D-cells | Somatostatin |
| K-cells | Glucose-dependent Insulinotropic Polypeptide |
| L-cells | GLP-1 |
|  | GLP-2 |
| I-cells | Cholycystokinin |
| Mo-cells | Motilin |
| Gr-cells | Ghrelin |

Chitosan-Based Nanoparticles

By "chitosan-based nanoparticle", or "DNA/chitosan particle" is meant a complex comprising a plurality of chitosan polymers and a DNA molecule. "Polyplex" is used interchangeably with "chitosan-based nanoparticle" herein. The chitosan polymers of chitosan-based nanoparticles preferably have an average molecular weight of less than about 250 kDa. The DNA molecule in the context of the chitosan-based nanoparticle is deliverable to a cell in vivo. Frequently, a chitosan-based nanoparticle is referred to herein as a nanoparticle.

As used herein, average weight of chitosan polymers refers to the weight average molecular weight.

In one embodiment, chitosan is obtained by the method of Richardson et al., Int. J. Pharmaceutics, 178:231-243, 1999.

In one embodiment, high molecular weight chitosan-based nanoparticles are produced as follows. Plasmid DNA and chitosan solutions, prepared separately, are adjusted to a concentration equal to two-times the required final concentration. DNA is diluted in water or 50 mM sodium sulfate solution. A desired molecular weight chitosan polymer preparation, which comprises chitosan polymers preferably having an average molecular weight less than 250 kDa, is dissolved in 5 mM sodium acetate, pH5.5. Both solutions are incubated at 55° C. for 5 minutes before being combined to form a chitosan-based nanoparticle preparation mixture. Equal volumes of the two solutions are mixed and rapidly vortexed for 30 seconds to form DNA/chitosan particles. This preparation may be further diluted in various buffers prior to use. Production of the nanoparticles of the invention does not require lyophilization and use of lyophilized product in an acetylation reaction.

In a preferred embodiment, chitosan-based nanoparticles, especially low molecular weight chitosan-based nanoparticles, are produced as follows. Chitosan powder is added to 0.5% aqueous solution of acetic acid until the chitosan working solution reaches pH 4.8. The working solution is then filtered through a membrane filter (Acrodisc 0.2 μm pore size, Pall Life Sciences). Stock DNA solutions (in 1×TE) of plasmid A and plasmid B are mixed in a 5:1 ratio of plasmid A to plasmid B, diluted in water, and then filtered through a membrane filter (Acrodisc 0.2 μm pore size, Pall Life Sciences) to produce the DNA working solution. See the experimental section for further details.

The chitosan polymers of chitosan-based nanoparticles preferably have an average molecular weight of less than about 250 kDa, more preferably less than 230 kDa, more preferably less than 220 kDa. In a preferred embodiment, the plurality of chitosan polymers of the nanoparticle have an average molecular weight from about 3 kDa to about 250 kDa. Other ranges of average molecular weight for chitosan polymers in preferred nanoparticles of the invention include 3-6 kDa, 3-10 kDa, 3-50 kDa, 3-210 kDa, 10-210 kDa, 10-250 kDa, and 210-250 kDa.

A preferred DNA concentration in the chitosan-based nanoparticle preparation mixture is in the range of about 1 µg/ml to about 1.5 mg/ml, more preferably between about 10 µg/ml to about 1 mg/ml, more preferably between about 25 µg/ml to about 1 mg/ml, more preferably between about 50 µg/ml to about 1 mg/ml, more preferably between about 100 µg/ml to about 1 mg/ml.

A preferred chitosan concentration in the chitosan-based nanoparticle preparation mixture is in the range of 0.001% to 1.0%, w/w.

In a preferred embodiment, the chitosan-based nanoparticle has an amine:phosphate (N:P) ratio from about 1:1 to about 100:1. Other N:P ratio ranges of preferred chitosan-based nanoparticles of the invention include about 1:1 to about 6:1, about 1:1 to about 4:1, about 10:1 to about 90:1, about 10:1 to about 50:1, about 10:1 to about 40:1, about 10:1 to about 30:1, about 60:1 to about 100:1, and about 70:1 to about 100:1.

The amine content of chitosan may be varied by varying the degree of chitosan acetylation. The chitosan polymers used in the chitosan-based nanoparticles of the invention preferably have between 70% and 100%, more preferably between 80% and 100%, more preferably between 90% and 100% deacetylation.

In a preferred embodiment, the chitosan-based nanoparticle has a chitosan:nucleic acid w/w ratio from about 1:1 to about 50:1. Other chitosan:nucleic acid w/w ratio ranges of preferred chitosan-based nanoparticles include about 1:1 to about 5:1, about 1:1 to about 3:1, about 5:1 to about 45:1, about 5:1 to about 25:1, about 5:1 to about 20:1, about 5:1 to about 15:1, about 30:1 to about 50:1, and about 35:1 to about 50:1.

In a preferred embodiment, the composition comprises nanoparticles having an average zeta potential between +5 mV and +50 mV at a pH of 5.

In another preferred embodiment, the composition comprises nanoparticles having an average zeta potential between +30 mV and +50 mV at a pH of 5.

In another preferred embodiment, the composition comprises nanoparticles having an average zeta potential between +30 mV and +40 mV at a pH of 5.

In another preferred embodiment, the composition comprises nanoparticles having an average zeta potential between +32 mV and +40 mV at a pH of 5.

In another preferred embodiment, the composition comprises nanoparticles having an average zeta potential between +5 mV and +25 mV at a pH of 5.

In another preferred embodiment, the composition comprises nanoparticles having an average zeta potential between +5 mV and +8 mV at a pH of 5.

In a preferred embodiment, the composition comprises nanoparticles having an average diameter less than 225 nm.

In another preferred embodiment, the composition comprises nanoparticles having an average diameter between 80 nm and 225 nm.

In another preferred embodiment, the composition comprises nanoparticles having an average diameter between 80 nm and 175 nm.

In a preferred embodiment, the composition has a DNA concentration of between about 1 µg/ml and about 1.5 mg/ml, more preferably between about 1 µg/ml and about 1 mg/ml, more preferably between about 10 µg/ml and about 1 mg/ml, more preferably between about 50 µg/ml and about 1 mg/ml, more preferably between about 100 µg/ml and about 1 mg/ml, more preferably between about 150 µg/ml and about 1 mg/ml, more preferably between about 200 µg/ml and about 1 mg/ml.

In a preferred embodiment, the composition has a pH of less than 6.5, more preferably less than 6.0, and most preferably between about 4.5 and about 5.5.

In a preferred embodiment, the chitosan polymers of the nanoparticle have a degree of deacetylation greater than about 70%, more preferably greater than about 75%, more preferably greater than about 80%, more preferably greater than about 85%, more preferably greater than about 90%, more preferably greater than about 95%, and most preferably at least 98%.

In a preferred embodiment, the composition comprises low molecular weight chitosan nanoparticles, wherein the plurality of chitosan polymers of the low molecular weight nanoparticles have an average molecular weight between 3 kDa and 25 kDa. In a preferred embodiment, low molecular weight chitosan nanoparticles have an N:P ratio between 10:1 and 90:1. In a preferred embodiment, low molecular weight chitosan nanoparticles have an average zeta potential between +30 mV and +50 mV, more preferably between +30 mV and +40 mV at a pH of 5. In a preferred embodiment, low molecular weight chitosan nanoparticles have an average diameter less than 175 nm.

In another embodiment, the composition comprises high molecular weight chitosan nanoparticles, wherein the plurality of chitosan polymers of the high molecular weight nanoparticles have an average molecular weight between 25 kDa and 250 kDa. In a preferred embodiment, high molecular weight chitosan nanoparticles have an N:P ratio between 2:1 and 40:1. In a preferred embodiment, high molecular weight chitosan nanoparticles have an average zeta potential between +5 mV and +25 mV at a pH of 5. In a preferred embodiment, high molecular weight chitosan nanoparticles have an average diameter less than 225 nm. In a preferred embodiment, high molecular weight chitosan nanoparticles have a chitosan:nucleic acid w/w ratio between 1:1 and 30:1.

In an especially preferred embodiment, the plurality of chitosan polymers of the nanoparticle have an average molecular weight of about 3.9 kDa, and a degree of deacetylation of about 98%. In a preferred embodiment, the composition comprises nanoparticles having an average diameter less than 175 nm. In a preferred embodiment, the composition has a DNA concentration of between about 25 µg/ml and about 100 µg/ml. In a preferred embodiment, the nanoparticle has an N:P ratio of between about 40:1 and about 80:1, most preferably an N:P ratio of about 60:1. In a preferred embodiment, the nanoparticle has a chitosan:nucleic acid w/w ratio between 20:1 and 40:1, most preferably a w/w ratio of 30:1.

In a further preferred embodiment, the plurality of chitosan polymers of the nanoparticle have an average molecular weight of about 3.9 kDa, and a degree of deacetylation of about 98%. In a preferred embodiment, the composition comprises nanoparticles having an average diameter of less than 175 nm. In a preferred embodiment, the composition has a DNA concentration of between about 200 µg/ml and about 1 mg/ml. In a preferred embodiment, the nanoparticle has an N:P ratio of between about 10:1 and about 30:1, most preferably an N:P ratio of about 20:1. In a preferred embodiment, the nanoparticle has a chitosan:nucleic acid w/w ratio between 5:1 and 15:1, most preferably a w/w ratio of 10:1.

Procedures or features that may be used or added to alter transfection efficiency include co-complexation of lysosomolytic agents in nanoparticles, though lysosomolytic agents are not required. Combination nanoparticles that include additional therapeutic agents co-complexed are contemplated. These additional agents and lysosomolytic agents may be co-complexed during complex formation.

Additionally, the stability of nanoparticles may be varied by crosslinking.

Additionally, ligands or targeting moieties may be conjugated or otherwise affixed to nanoparticles to enhance specificity or uptake, for example, by receptor-mediated endocytosis.

In a number of preferred embodiments, a chitosan-based nanoparticle of the invention is capable of producing long-term expression of a therapeutic nucleic acid in a gut mucosal cell. Differentiated gut mucosal cells are typically short-lived. As used herein, long-term expression in a mucosal cell refers to expression in one or more mucosal cells, and expression in the mucosa is preferably for more than about 4 days. Without being bound by theory, in the context of the small intestine, which is a preferred location for mucosal cell transfection in the present invention, a nanoparticle of the invention may enter a crypt of the gut mucosa and transfect a gut mucosal precursor cell. This provides for long-term expression of a therapeutic nucleic acid relative to transfection of a terminally differentiated and shorter-lived mucosal cell. Additionally, in embodiments wherein a therapeutic construct comprises an integration sequence, the nanoparticle provides for genomic integration of the therapeutic nucleic acid into the genome of a precursor cell (including stem cells) and, in a preferred embodiment, long-term expression of a therapeutic nucleic acid in a series of differentiated mucosal cells arising from the precursor cell. Accordingly, as used herein, long-term expression in a mucosal cell does not necessarily refer to expression in the same cell for the duration.

In some embodiments, the expression control region of a therapeutic construct possesses constitutive activity, providing for the static expression of a therapeutic nucleic acid. In a number of preferred embodiments, the expression control region of a therapeutic construct does not have constitutive activity. This provides for the dynamic expression of a therapeutic nucleic acid. By "dynamic" expression is meant expression that changes over time. Such expression over time can include a period of no expression or undetectable expression, during which a therapeutic nucleic acid is present in a mucosal cell but is not expressed or is not expressed at a detectable level. Dynamic expression may include several such periods of low or absent expression separated by periods of detectable expression. In a number of preferred embodiments, the therapeutic nucleic acid is operably linked to a regulatable promoter. This provides for the regulatable expression of therapeutic nucleic acids.

The ability to produce long-term expression of a therapeutic nucleic acid is an identifying characteristic of many preferred chitosan-based nanoparticles of the invention. The ability to produce long-term expression refers to the ability of a preferred nanoparticle to produce long-term expression after a single administration, although some methods herein involve repeated administrations of chitosan-based nanoparticles. Notably, in embodiments wherein a nanoparticle is capable of producing long-term expression of a therapeutic nucleic acid, the long-term expression of such a therapeutic nucleic acid may be dynamic, with periods of low or undetectable expression.

Expression Control Regions

Expression control regions comprise regulatory polynucleotides (sometimes referred to herein as elements), such as promoters and enhancers, that influence expression of an operably linked therapeutic nucleic acid. Preferred expression control regions are those that are selectively active in gut tissue or a particular gut tissue cell type.

In a number of preferred embodiments, an expression control region of a therapeutic construct comprises a gut-specific promoter. A gut-specific promoter exhibits activity in gut mucosal cells and potentially other gut cells. In a preferred embodiment, a gut-specific promoter does not exhibit substantial activity in a wide variety of other tissues. Viral promoters such as the CMV promoter which exhibit activity in a wide variety of cell types are not gut-specific promoters. Gut specific promoters may exhibit constitutive or non-constitutive activity. Especially preferred are regulatable gut-specific promoters.

For example, the promoter of the proglucagon gene comprises gut-specific elements and finds use in the present invention (Lee, Y. C., et al. J. Biol. Chem. 267:10705 (1992); Gajic and Drucker, Endocrinol. 132:1055 (1993).

In a number of preferred embodiments, an expression control region of a therapeutic construct comprises a gut mucosal cell-specific promoter. A gut mucosal cell-specific promoter exhibits activity in gut mucosal cells. In a preferred embodiment, a gut mucosal cell-specific promoter does not exhibit substantial activity in other gut cells or in a wide variety of other tissues.

In a number of preferred embodiments, an expression control region of a therapeutic construct comprises a gut endocrine cell-specific promoter. Especially preferred are regulatable endocrine cell-specific promoters. The GIP promoter is a specific example of a regulatable gut endocrine cell promoter (see U.S. Ser. No. 09/804,409 which is expressly incorporated herein in it's entirety by reference). The GIP-promoter is glucose-regulatable and can confer glucose-regulatable endocrine cell-specific expression to an operably linked therapeutic nucleic acid.

Additional examples of gut-specific promoters that may be employed in the invention are listed in Table 2. Many of these promoters are also regulatable. This list is merely exemplary and is not intended to be exhaustive of all the possible gut-specific promoters useful in the invention.

TABLE 2

Exemplary Promoters and Enhancers for Targeting Expression of Proteins to Endocrine Cells in the Gut
Exemplary Promoters and Enhancers for Targeting Expression of Proteins to Endocrine Cells in the Gut Glucokinase
Chromogranin A and B
Glucose-dependent Insulinotropic Polypeptide
Cholycystokinin
Proglucagon
Adenosine deaminase
Secretin
Gastrin
Somatostatin
Motilin
Ghrelin
Sucrose-isomaltase Preferred expression control regions confer regulatable expression to an operably linked therapeutic nucleic acid. A signal (sometimes referred to as a stimulus) can increase or decrease expression of a therapeutic nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

Numerous regulatable promoters are known in the art. Preferred inducible expression control regions include those comprising an inducible promoter that is stimulated with a small molecule chemical compound. In one embodiment, an expression control region is responsive to a chemical that is orally deliverable but not normally found in food. Particular examples can be found, for example, in U.S. Pat. Nos. 5,989,910; 5,935,934; 6,015,709; and 6,004,941.

A particularly preferred expression control region is one that increases or decreases expression of an operably linked therapeutic nucleic acid in response to the presence of a nutrient, in which case the expression control region is referred to as "nutrient-regulatable." A nutrient-regulatable expression control region generally provides basal levels of transcription in the absence of the nutrient. Typically, basal levels of transcription are greater for a repressible element than for an inducible element.

The term "nutrient" is used broadly to refer to any of the organic or inorganic substances present in ingestible or consumable material. Particular examples of nutrients include sugars (e.g., glucose, lactose, sucrose, fructose, mannose, etc.), carbohydrates, starches, fats (saturated or unsaturated), lipids, fatty acids, triglycerides, polypeptides, amino acids, cellulose, hormones, vitamins, and minerals.

Nutrient-regulatable expression control regions exist, for example, as promoters that regulate expression of enzymes involved in glycolysis, lipid metabolism, carbohydrate metabolism and cholesterol (e.g., steroid) metabolism, which are modulated by sugars, fats, carbohydrate, and cholesterol, respectively, and are applicable in the invention. Particular examples of nutrient-regulatable elements are glucose inducible elements that drive expression of L-pyruvate kinase, acetyl-CoA-carboxylase, spot-14, fatty acid synthase, glyceraldehyde phosphate dehydrogenase phospho-enol-pyruvate carboxykinase, glucose-6-phosphatase and phosphofructokinase (see, also, e.g., Rutter, G A et al., News Physiol Sci. 15:149 (2000)). Another example of a nutrient-regulatable element is the alcohol-dehydrogenase gene regulatory element. Yet another example of a nutrient-regulatable element is the vitamin-D response element, which confers expression in the presence of vitamin D. The mammalian metallothionein gene promoter is an expression control element inducible by metals. As with tissue-specific control elements, nutrient-regulatable control elements may be responsive to multiple nutrients. For example, a glucose-inducible element may also be responsive to lactose. A particular nutrient (e.g., glucose) is therefore not meant to be exclusive of other nutrients in that other nutrients may modulate activity (increase or decrease), to a lesser degree, of the control element.

Expression control elements included herein can be from bacteria, yeast, plant, or animal (mammalian or non-mammalian). Thus, any expression control element from any organism that is inducible by a signal (e.g., nutrient) in the context of a mammalian gut mucosal cell, preferably a human gut mucosal cell, can be used.

Expression control regions include full-length promoter sequences, such as native promoter and enhancer elements, as well as subsequences or polynucleotide variants which retain all or part of full-length or non-variant function (e.g., retain some amount of nutrient regulation or cell/tissue-specific expression). As used herein, the term "functional" and grammatical variants thereof, when used in reference to a nucleic acid sequence, subsequence or fragment, means that the sequence has one or more functions of native nucleic acid sequence (e.g., non-variant or unmodified sequence). As used herein, the term "variant" means a sequence substitution, deletion, or addition, or other modification (e.g., chemical derivatives such as modified forms resistant to nucleases).

As used herein, the term "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

In a number of preferred embodiments, the therapeutic nucleic acid of the nanoparticle encodes a therapeutic protein. In an especially preferred embodiment, the therapeutic protein is a secreted therapeutic protein. Preferably, the nanoparticle is capable of increasing the systemic level of the secreted therapeutic protein. Preferably, the nanoparticle is capable of producing a long-term increase in the systemic level of the secreted therapeutic protein. In one embodiment, the long-term increase in the systemic level of secreted therapeutic protein is static. In a preferred embodiment, the long-term increase in the systemic level of secreted therapeutic protein is dynamic.

It will be appreciated that dynamic levels of therapeutic protein may be achieved with constitutive as well as non-constitutive expression control regions. In a number of preferred embodiments, therapeutic protein is stored in gut endocrine cells and released in response to a signal, thereby producing a dynamic systemic level of therapeutic protein irrespective of whether transcriptional activity is constitutive or non-constitutive.

Integration

In a number of preferred embodiments, a chitosan-based nanoparticle comprises a therapeutic construct that comprises (i) a therapeutic nucleic acid operably linked to an expression control region, and (ii) an integration sequence. The integration sequence provides for integration of the therapeutic nucleic acid operably linked to the expression control region, taken together, into the genome of a gut mucosal cell. Such a therapeutic construct, when combined in a gut mucosal cell with a means for integration, yields a gut mucosal cell with a modified genome carrying the heterologous expression control sequence operably linked to a therapeutic nucleic acid. Accordingly, such nanoparticles provide for the production of gut mucosal cells comprising heterologous expression control sequences operably linked to therapeutic nucleic acids. Long-term expression extending weeks and even months may be achieved with such nanoparticles.

Numerous means for integration, and integration sequences that function therewith, are known in the art (see for example Nunes-Duby et al., Nucleic Acids Res. 26:391-406, 1998; Sadwoski, J. Bacteriol., 165:341-357, 1986; Bestor, Cell, 122(3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al, Cell, 29:227-234, 1982) R (Matsuzaki, et al, J. Bacteriology, 172:610-618, 1990), φC31

(see for example Groth et al., J. Mol. Biol. 335:667-678, 2004; Calos, Curr Gene Ther., 6:633-45, 2006), sleeping beauty, transposases of the mariner family (Plasterk et al, supra), and means from integrating viruses such as AAV, retroviruses, and lentiviruses having components that provide for virus integration such as the LTR sequences of retroviruses or lentivirus and the ITR sequences of AAV (Kootstra et al., Ann. Rev. Pharm. Toxicol., 43:413-439, 2003).

In one embodiment, a therapeutic construct comprises a single integration sequence operably linked to the therapeutic nucleic acid-expression control region polynucleotide. In another embodiment, a therapeutic construct comprises a first and a second integration sequence, which are operably linked to the therapeutic nucleic acid-expression control region polynucleotide. In the methods herein, the means for integration and the type of integration sequence used are compatible.

In a number of preferred embodiments, a chitosan-based nanoparticle comprises a non-therapeutic construct, which non-therapeutic construct comprises a nucleic acid encoding a means for integration. An integration sequence operably linked to a therapeutic nucleic acid-expression control region polynucleotide, when combined in a cell with a means for integration, provides for genomic insertion of the therapeutic nucleic acid-expression control region polynucleotide.

Therapeutic Nucleic Acids

As used herein, therapeutic nucleic acids are nucleic acids capable of exerting a therapeutic effect when expressed in a gut mucosal cell. The therapeutic effect exerted by a therapeutic nucleic acid need not be in gut tissue.

Therapeutic nucleic acids include nucleic acids encoding therapeutic proteins, as well as nucleic acids that produce transcripts that are therapeutic RNAs. A therapeutic RNA is an RNA molecule capable of exerting a therapeutic effect in a mammalian cell. Therapeutic RNAs include antisense RNAs, siRNAs, short hairpin RNAs, and enzymatic RNAs.

As used herein, therapeutic nucleic acids that encode therapeutic proteins include nucleic acids that encode proprotein forms of therapeutic proteins that require processing, e.g., proteolytic processing by a convertase, for activity.

In one embodiment, a therapeutic nucleic acid does not encode a food allergen. By food allergen is meant a food allergen protein that causes a hypersensitivity reaction. Generally, the use of nucleic acids encoding such food allergen proteins is undesirable because of the potentially lethal consequences of expression.

In one embodiment, a therapeutic nucleic acid encodes an immunogen that is capable of eliciting a specific antibody response and/or T cell response to the immunogen. Preferably, the immunogen is capable of eliciting a therapeutic immune response.

The nature of therapeutic proteins and encoding therapeutic nucleic acids that are useful in the present invention is not constrained by the chitosan-based nanoparticles of the invention. A wide variety of therapeutic nucleic acids of wide ranging sizes are contemplated for use. Especially preferred for use in the invention are therapeutic nucleic acids encoding secretable therapeutic proteins, which may be secreted into the blood circulatory system by gut endocrine cells.

As used herein, the term "produces" or "production," when used in reference to a secreted therapeutic protein refers to expression or secretion of the protein by a gut mucosal cell. In some embodiments, a signal or stimuli (i.e., a secretagogue) stimulates release into the systemic circulation of a secretable therapeutic protein already present in the cell.

In some preferred embodiments, a therapeutic nucleic acid encoding a secreted therapeutic protein is expressed in a gut endocrine cell (e.g., K-cell, L-cell, etc.). The expression control region used to confer expression of the therapeutic protein may or may not be regulatable, but in either case a signal typically will regulate secretion of the protein from the cell into the blood. In this case, the signal or stimuli functions as a secretagogue that stimulates or increases secretion of a protein.

In one embodiment, therapeutic nucleic acids are engineered to encode secretable proforms of therapeutic proteins that are not processed within gut cells. Rather, these proforms (protherapeutics) are activated in the vicinity of target tissues.

Methods and therapeutic nucleic acids for the treatment of diseases associated with gut mucosa are also contemplated by the present invention. For example, compositions and methods for the treatment of cancer and/or inflammation associated with gut mucosa are contemplated.

Therapeutic proteins contemplated for use in the invention have a wide variety of activities and find use in the treatment of a wide variety of disorders. The following description of therapeutic protein activities, and indications treatable with therapeutic proteins of the invention, is exemplary and not intended to be exhaustive. The term "subject" refers to an animal, with mammals being preferred, and humans being especially preferred.

A partial list of therapeutic proteins and target diseases is shown in Table 3.

TABLE 3

| LEAD COMPOUNDS | TARGET DISEASE | FUNCTION | THERAPEUTIC EFFECT |
| --- | --- | --- | --- |
| Insulin | Diabetes | Insulin replacement | Improve glucose tolerance. Delay/prevent diabetes. |
| Glucagon antagonists | Diabetes | Reduce endogenous glucose production | Improve glucose tolerance |
| GLP-1 | Diabetes Obesity | Stimulate growth of β-cells, improve insulin sensitivity, suppress appetite | Improve glucose tolerance. Induce weight loss |
| Leptin | Obesity Diabetes | Appetite suppression and improvement of insulin sensitivity | Induce weight loss. Improve glucose tolerance |
| CCK | Obesity | Appetite suppression | Induce weight loss |
| Growth Hormone (GH) | GH deficiencies, wasting and anti-aging | GH replacement | Improve growth |
| Clotting factors | Hemophilia | Clotting factors replacement | Improve clotting time |

TABLE 3-continued

| LEAD COMPOUNDS | TARGET DISEASE | FUNCTION | THERAPEUTIC EFFECT |
|---|---|---|---|
| Therapeutic antibodies and antibody fragments/portions | Infections Cancer | Pathogen neutralization or immune modulations | Prevent infections or transplant rejections |
| inflammation inhibitors, e.g., IL-10, TNFα antagonists, IL-17 antagonists | GI tract inflammation; e.g., inflammatory bowel disease | immune modulation | prevent inflammation in GI tract |

Hyperglycemia and Body Mass

Therapeutic proteins include insulin and insulin analogs. Diabetes mellitus is a debilitating metabolic disease caused by absent (type 1) or insufficient (type 2) insulin production from pancreatic β-cells (Unger, R. H. et al., Williams Textbook of Endocrinology Saunders, Philadelphia (1998)). Beta-cells are specialized endocrine cells that manufacture and store insulin for release following a meal (Rhodes, et. al. J. Cell Biol. 105:145 (1987)) and insulin is a hormone that facilitates the transfer of glucose from the blood into tissues where it is needed. Patients with diabetes must frequently monitor blood glucose levels and many require multiple daily insulin injections to survive. However, such patients rarely attain ideal glucose levels by insulin injection (Turner, R. C. et al. JAMA 281:2005 (1999)). Furthermore, prolonged elevation of insulin levels can result in detrimental side effects such as hypoglycemic shock and desensitization of the body's response to insulin. Consequently, diabetic patients still develop long-term complications, such as cardiovascular diseases, kidney disease, blindness, nerve damage and wound healing disorders (UK Prospective Diabetes Study (UKPDS) Group, Lancet 352, 837 (1998)).

Disorders treatable by a method of the invention include a hyperglycemic condition, such as insulin-dependent (type 1) or -independent (type 2) diabetes, as well as physiological conditions or disorders associated with or that result from the hyperglycemic condition. Thus, hyperglycemic conditions treatable by a method of the invention also include a histopathological change associated with chronic or acute hyperglycemia (e.g., diabetes). Particular examples include degeneration of pancreas (β-cell destruction), kidney tubule calcification, degeneration of liver, eye damage (diabetic retinopathy), diabetic foot, ulcerations in mucosa such as mouth and gums, excess bleeding, delayed blood coagulation or wound healing and increased risk of coronary heart disease, stroke, peripheral vascular disease, dyslipidemia, hypertension and obesity.

Thus, in various methods of the invention, a gut mucosal cell that produces insulin or a functional subsequence of insulin or an analog of insulin in response to glucose is useful for decreasing glucose, improving glucose tolerance, treating a hyperglycemic condition (e.g., diabetes) or for treating a physiological disorders associated with or resulting from a hyperglycemic condition. Such disorders include, for example, diabetic neuropathy (autonomic), nephropathy (kidney damage), skin infections and other cutaneous disorders, slow or delayed healing of injuries or wounds (e.g., that lead to diabetic carbuncles), eye damage (retinopathy, cataracts) which can lead to blindness, diabetic foot and accelerated periodontitis. Such disorders also include increased risk of developing coronary heart disease, stroke, peripheral vascular disease, dyslipidemia, hypertension and obesity.

As used herein, the term "hyperglycemic" or "hyperglycemia," when used in reference to a condition of a subject, means a transient or chronic abnormally high level of glucose present in the blood of a subject. The condition can be caused by a delay in glucose metabolization or absorption such that the subject exhibits glucose intolerance or a state of elevated glucose not typically found in normal subjects (e.g., in glucose-intolerant subdiabetic subjects at risk of developing diabetes, or in diabetic subjects). Fasting plasma glucose (FPG) levels for normoglycemia are less than about 110 mg/dl, for impaired glucose metabolism, between about 110 and 126 mg/di, and for diabetics greater than about 126 mg/dl.

Disorders treatable by producing a protein in a gut mucosal tissue also include obesity or an undesirable body mass. Leptin, cholecystokinin, PYY and GLP-1 decrease hunger, increase energy expenditure, induce weight loss or provide normal glucose homeostasis. Thus, in various embodiments, a method of the invention for treating obesity or an undesirable body mass, or hyperglycemia, involves the use of a therapeutic nucleic acid encoding leptin, cholecystokinin, PYY or GLP-1. Disorders treatable also include those typically associated with obesity, for example, abnormally elevated serum/plasma LDL, VLDL, triglycerides, cholesterol, plaque formation leading to narrowing or blockage of blood vessels, increased risk of hypertension/stroke, coronary heart disease, etc.

As used herein, the term "obese" or "obesity" refers to a subject having at least a 30% increase in body mass in comparison to an age and gender matched normal subject. "Undesirable body mass" refers to subjects having 1%-29% greater body mass than a matched normal subject as well as subjects that are normal with respect to body mass but who wish to decrease or prevent an increase in their body mass.

In one embodiment, a therapeutic protein of the invention is a glucagon antagonist. Glucagon is a peptide hormone produced by α-cells in pancreatic islets and is a major regulator of glucose metabolism (Unger R. H. & Orci L. N. Eng. J. Med. 304:1518 (1981); Unger R. H. Diabetes 25:136 (1976)). As with insulin, blood glucose concentration mediates glucagon secretion. However, in contrast to insulin glucagon is secreted in response to a decrease in blood glucose. Therefore, circulating concentrations of glucagon are highest during periods of fast and lowest during a meal. Glucagon levels increase to curtail insulin from promoting glucose storage and stimulate liver to release glucose into the blood. A specific example of a glucagon antagonist is [des-His$^1$, des-Phe$^6$, Glu$^9$]glucagon-NH$_2$. In streptozotocin diabetic rats, blood glucose levels were lowered by 37% within 15 min of an intravenous bolus (0.75 µg/g body weight) of this glucagon antagonist (Van Tine B. A. et. al. Endocrinology 137:3316 (1996)).

In another embodiment, a therapeutic protein of the invention useful for treating a hyperglycemic condition or undesirable body mass (e.g., obesity) is a glucagon-like peptide-1 (GLP-1). GLP-1 is a hormone released from L-cells in the intestine during a meal which stimulates pancreatic β-cells to increase insulin secretion. GLP-1 has additional activities which make it an attractive therapeutic agent for treating obesity and diabetes. For example, GLP-1 reduces gastric emptying, suppresses appetite, reduces glucagon concentration, increases .beta.-cell mass, stimulates insulin biosynthesis and secretion in a glucose-dependent fashion, and likely increases tissue sensitivity to insulin (Kieffer T. J., Habener J. F. Endocrin. Rev. 20:876 (2000)). Therefore, regulated release of GLP-1 in the gut to coincide with a meal can provide therapeutic benefit for a hyperglycemic condition or an undesirable body mass. GLP-1 analogs that are resistant to dipeptidyl peptidate IV (DPP IV) provide longer duration of action and improved therapeutic value. Thus, GLP-1 analogs are preferred therapeutic polypeptides.

In another embodiment, a therapeutic protein of the invention useful for treating a hyperglycemic condition is an antagonist to the hormone resistin. Resistin is an adipocyte-derived factor for which expression is elevated in diet-induced and genetic forms of obesity. Neutralization of circulating resistin improves blood glucose and insulin action in obese mice. Conversely, administration of resistin in normal mice impairs glucose tolerance and insulin action (Steppan C M et. al. Nature 409:307 (2001)). Production of a protein that antagonizes the biological effects of resistin in gut can therefore provide an effective therapy for obesity-linked insulin resistance and hyperglycemic conditions.

In another embodiment, a therapeutic polypeptide of the invention useful for treating a hyperglycemic condition or undesirable body mass (e.g., obesity) is leptin. Leptin, although produced primarily by fat cells, is also produced in smaller amounts in a meal-dependent fashion in the stomach. Leptin relays information about fat cell metabolism and body weight to the appetite centers in the brain where it signals reduced food intake (promotes satiety) and increases the body's energy expenditure.

In another embodiment, a therapeutic polypeptide of the invention useful for treating a hyperglycemic condition or undesirable body mass (e.g., obesity) is the C-terminal globular head domain of adipocyte complement-related protein (Acrp30). Acrp30 is a protein produced by differentiated adipocytes. Administration of a proteolytic cleavage product of Acrp30 consisting of the globular head domain to mice leads to significant weight loss (Fruebis J. et al. Proc. Natl. Acad. Sci. USA 98:2005 (2001)).

In another embodiment, a therapeutic polypeptide of the invention useful for treating a hyperglycemic condition or undesirable body mass (e.g., obesity) is cholecystokinin (CCK). CCK is a gastrointestinal peptide secreted from the intestine in response to particular nutrients in the gut. CCK release is proportional to the quantity of food consumed and is believed to signal the brain to terminate a meal (Schwartz M. W. et. al. Nature 404:661-71 (2000)). Consequently, elevated CCK can reduce meal size and promote weight loss or weight stabilization (i.e., prevent or inhibit increases in weight gain).

Regarding PYY, see for example le Roux et al., Proc Nutr Soc. 2005 May; 64(2):213-6.

Immunological Disorders

In one embodiment, a therapeutic protein of the invention possesses immunomodulatory activity. For example, a therapeutic polypeptide of the present invention may be useful in treating deficiencies or disorders of the immune system, by activating or inhibiting the proliferation, differentiation, or mobilization (chemotaxis) of immune cells. Immune cells develop through the process of hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g. by chemotherapy or toxins), or infectious.

A therapeutic polypeptide of the present invention may be useful in treating deficiencies or disorders of hematopoietic cells. A therapeutic polypeptide of the present invention could be used to increase differentiation or proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

A therapeutic polypeptide of the present invention may also be useful in treating autoimmune disorders. Many autoimmune disorders result from inappropriate recognition of self as foreign material by immune cells. This inappropriate recognition results in an immune response leading to the destruction of the host tissue. Therefore, the administration of a therapeutic polypeptide of the present invention that inhibits an immune response, particularly the proliferation, differentiation, or chemotaxis of T-cells, may be an effective therapy in preventing autoimmune disorders.

Examples of autoimmune disorders that can be treated by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin-dependent diabetes mellitis, Crohn's disease, ulcerative colitis, and autoimmune inflammatory eye disease.

Similarly, allergic reactions and conditions, such as asthma (particularly allergic asthma) or other respiratory problems, may also be treated by a therapeutic polypeptide of the present invention. Moreover, these molecules can be used to treat anaphylaxis, hypersensitivity to an antigenic molecule, or blood group incompatibility.

A therapeutic polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a therapeutic polypeptide of the present invention that inhibits an immune response, particularly the proliferation, differentiation, or chemotaxis of T-cells, may be an effective therapy in preventing organ rejection or GVHD.

Similarly, a therapeutic polypeptide of the present invention may also be used to modulate inflammation. For example, the therapeutic polypeptide may inhibit the proliferation and differentiation of cells involved in an inflammatory response. These molecules can be used to treat inflammatory conditions, both chronic and acute conditions, including inflammation associated with infection (e.g. septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g. TNF or IL-1.)

Clotting Disorders

In some embodiments, a therapeutic polypeptide of the present invention may also be used to modulate hemostatic (the stopping of bleeding) or thrombolytic activity (clot formation). For example, by increasing hemostatic or thrombolytic activity, a therapeutic polypeptide of the present invention could be used to treat blood coagulation disorders (e.g. afibrinogenemia, factor deficiencies), blood platelet disorders (e.g. thrombocytopenia), or wounds resulting from trauma, surgery, or other causes. Alternatively, a therapeutic polypeptide of the present invention that can decrease hemostatic or thrombolytic activity could be used to inhibit or dissolve clotting. These molecules could be important in the treatment of heart attacks (infarction), strokes, or scarring. In one embodiment, a therapeutic polypeptide of the invention is a clotting factor, useful for the treatment of hemophilia or other coagulation/clotting disorders (e.g., Factor VIII, IX or X)

Hyperproliferative Disorders

In one embodiment, a therapeutic protein of the invention is capable of modulating cell proliferation. Such a therapeutic polypeptide can be used to treat hyperproliferative disorders, including neoplasms.

Examples of hyperproliferative disorders that can be treated by a therapeutic polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated by a therapeutic polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

A therapeutic polypeptide produced in gut mucosa according to the present invention may inhibit the proliferation of the disorder through direct or indirect interactions. Delivery to the circulatory system provides for access of therapeutic protein to a wide variety of tissues. Alternatively, a therapeutic polypeptide of the present invention may stimulate the proliferation of other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as with a chemotherapeutic agent.

Infectious Disease

In one embodiment, a therapeutic polypeptide of the present invention can be used to treat infectious disease. For example, by increasing the immune response, particularly increasing the proliferation and differentiation of B and/or T cells, infectious diseases may be treated. The immune response may be increased by either enhancing an existing immune response, or by initiating a new immune response. Alternatively, the therapeutic polypeptide of the present invention may also directly inhibit the infectious agent, without necessarily eliciting an immune response.

Viruses are one example of an infectious agent that can cause disease or symptoms that can be treated by a therapeutic polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g. Paramyxoviridae, Morbillivirus, Rhabdoviridae), Orthomyxoviridae (e.g. Influenza), Papovaviridae, Parvoviridae, Picornaviridae, Poxyiridae (such as Smallpox or Vaccinia), Reoviridae (e.g. Rotavirus), Retroviridae (HTLV-I, HTLV-II, Lentivirus), and Togaviridae (e.g. Rubivirus). Viruses falling within these families can cause a variety of diseases or symptoms, including, but not limited to: arthritis, bronchiollitis, encephalitis, eye infections (e.g. conjunctivitis, keratitis), chronic fatigue syndrome, hepatitis (A, B, C, E, Chronic Active, Delta), meningitis, opportunistic infections (e.g. AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g. Kaposi's, warts), and viremia. A therapeutic polypeptide of the present invention can be used to treat any of these symptoms or diseases.

Similarly, bacterial or fungal agents that can cause disease or symptoms and that can be treated or detected by a therapeutic polypeptide of the present invention include, but are not limited to, the following Gram-Negative and Gram-positive bacterial families and fungi: Actinomycetales (e.g. *Corynebacterium, Mycobacterium, Norcardia*), *Aspergillosis*, Bacillaceae (e.g. *Anthrax, Clostridium*), Bacteroidaceae, *Blastomycosis, Bordetella, Borrelia, Brucellosis, Candidiasis, Campylobacter, Coccidioidomycosis, Cryptococcosis, Dermatocycoses*, Enterobacteriaceae (*Klebsiella, Salmonella, Serratia, Yersinia*), *Erysipelothrix, Helicobacter, Legionellosis, Leptospirosis, Listeria, Mycoplasmatales*, Neisseriaceae (e.g. *Acinetobacter, Gonorrhea, Menigococcal*), Pasteurellacea Infections (e.g. *Actinobacillus, Heamophilus, Pasteurella*), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g. AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, *Chlamydia*, Syphilis, Diphtheria, Leprosy, Paratuberculosis, *Tuberculosis*, Lupus, Botulism, gangrene, tetanus, impetigo, Rheumatic Fever, Scarlet Fever, sexually transmitted diseases, skin diseases (e.g. cellulitis, dermatocycoses), toxemia, urinary tract infections, wound infections. A therapeutic polypeptide of the present invention can be used to treat any of these symptoms or diseases.

Moreover, parasitic agents causing disease or symptoms that can be treated by a therapeutic polypeptide of the present invention include, but are not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g. dysentery, giardiasis), liver disease, lung disease, opportunistic infections (e.g. AIDS related), Malaria, pregnancy complications, and toxoplasmosis. A therapeutic polypeptide of the present invention can be used to treat any of these symptoms or diseases.

Regeneration

A therapeutic polypeptide of the present invention can be used to differentiate, proliferate, and attract cells, fostering to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated with the contribution of a therapeutic protein of the invention include organs (e.g. pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration incurs a small amount of scarring, or occurs without scarring. Regeneration also may include angiogenesis.

Moreover, a therapeutic polypeptide of the present invention may increase regeneration of tissues difficult to heal. For example, increased tendon/ligament regeneration would quicken recovery time after damage. A therapeutic polypeptide of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a therapeutic polypeptide of the present invention to proliferate and differentiate nerve cells. Diseases that could be treated using this method include central and peripheral nervous system diseases, neuropathies, or mechanical and traumatic disorders (e.g. spinal cord disorders, head trauma, cerebrovascular disease, and stoke). Specifically, diseases associated with peripheral nerve injuries, peripheral neuropathy (e.g. resulting from chemotherapy or other medical therapies), localized neuropathies, and central nervous system diseases (e.g. Alzheimer's disease, Parkinson's disease, Huntington's disease, amyotrophic lateral sclerosis, and Shy-Drager syndrome), could all be treated using therapeutic proteins of the present invention. With respect to CNS disorders, numerous means are known in the art for facilitating therapeutic access to brain tissue, including methods for disrupting the blood brain barrier, and methods of coupling therapeutic agents to moieties that provide for transport into the CNS. In one embodiment, a therapeutic nucleic acid is engineered so as to encode a fusion protein, which fusion protein comprises a transport moiety and a therapeutic protein.

Chemotaxis

In one embodiment, a therapeutic polypeptide of the present invention possesses a chemotaxis activity. A chemotaxic molecule attracts or mobilizes cells (e.g. monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A therapeutic polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a therapeutic polypeptide of the present invention may inhibit chemotactic activity. These molecules could also be used to treat disorders. Thus, a therapeutic polypeptide of the present invention could be used as an inhibitor of chemotaxis.

Especially preferred for use are protherapeutic proteins that are activated in the vicinity of target tissues.

Additional therapeutic polypeptides contemplated for use include, but are not limited to, growth factors (e.g., growth hormone, insulin-like growth factor-1, platelet-derived growth factor, epidermal growth factor, acidic and basic fibroblast growth factors, transforming growth factor-$\beta$, etc.), to treat growth disorders or wasting syndromes; and antibodies (e.g., human or humanized), to provide passive immunization or protection of a subject against foreign antigens or pathogens (e.g., *H. Pylori*), or to provide treatment of cancer, arthritis or cardiovascular disease; cytokines, interferons (e.g., interferon (INF), INF-$\alpha$2b and 2a, INF-$\alpha$N1, INF-$\beta$1b, INF-gamma), interleukins (e.g., IL-1 to IL-10), tumor necrosis factor (TNF-$\alpha$ TNF-$\beta$), chemokines, granulocyte macrophage colony stimulating factor (GM-CSF), polypeptide hormones, antimicrobial polypeptides (e.g., antibacterial, antifungal, antiviral, and/or antiparasitic polypeptides), enzymes (e.g., adenosine deaminase), gonadotrophins, chemotactins, lipid-binding proteins, filgastim (Neupogen), hemoglobin, erythropoietin, insulinotropin, imiglucerase, sarbramostim, tissue plasminogen activator (tPA), urokinase, streptokinase, phenylalanine ammonia lyase, brain-derived neurotrophic factor (BDNF), nerve growth factor (NGF), thrombopoietin (TPO), superoxide dismutase (SOD), adenosine deamidase, catalase calcitonin, endothelian, L-asparaginase pepsin, uricase trypsin, chymotrypsin elastase, carboxypeptidase lactase, sucrase intrinsic factor, calcitonin parathyroid hormone (PTH)-like, hormone, soluble CD4, and antibodies and/or antigen-binding fragments (e.g, FAbs) thereof (e.g., orthoclone OKT-e (anti-CD3), GPIIb/IIa monoclonal antibody).

Methods for Transfecting Gut Mucosal Cells

In one aspect, the invention provides methods for transfecting gut mucosal cells with therapeutic nucleic acids in vivo. The methods comprise contacting gut mucosa in vivo with a chitosan-based nanoparticle of the invention.

The methods are used to transfect gut mucosal cells in mammals. In a preferred embodiment, the mammal is a primate. In an especially preferred embodiment, the mammal is a human. In another embodiment, the mammal is a non-primate. Preferred non-primate mammals include dogs, cats and horses.

In a preferred embodiment, the method involves contacting mucosa of the small intestine. In a preferred embodiment, the method involves contacting mucosa of the duodenum, jejunum, or ileum with a chitosan-based nanoparticle of the invention.

In a preferred embodiment, the method involves contacting mucosa of the stomach with a chitosan-based nanoparticle of the invention.

In a preferred embodiment, the method involves contacting mucosa of the colon with a chitosan-based nanoparticle of the invention.

In a preferred embodiment, the chitosan-based nanoparticle transfects a gut mucosal precursor cell. In a preferred embodiment, the gut mucosal precursor cell is a gut endocrine cell precursor cell. In a preferred embodiment, the gut endocrine cell precursor cell produces a gut endocrine cell selected from the group consisting of K cells, L-cells, S-cells, G-cells, D-cells, I-cells, Mo-cells, and Gr-cells. In an especially preferred embodiment, the gut endocrine cell precursor cell produces a K cell.

In a preferred embodiment, the gut mucosal precursor cell is a mucosal cell of the small intestine. In a preferred embodiment, the gut mucosal precursor cell is a mucosal cell of the duodenum, jejunum, or ileum.

In a preferred embodiment, the gut mucosal precursor cell is a mucosal cell of the stomach.

In a preferred embodiment, the gut mucosal precursor cell is a mucosal cell of the colon.

In a preferred embodiment, the gut mucosal precursor cell produces a mucosal cell that expresses the therapeutic nucleic acid.

In one embodiment, the therapeutic nucleic acid encodes a therapeutic RNA.

In a preferred embodiment, the therapeutic nucleic acid encodes a therapeutic protein. In a preferred embodiment, the therapeutic protein is a secreted therapeutic protein.

In a preferred embodiment, the therapeutic nucleic acid of the nanoparticle encodes a therapeutic protein that is selected from the group consisting of hormones, enzymes, cytokines, chemokines, antibodies, mitogenic factors, growth factors, differentiation factors, factors influencing angiogenesis, factors influencing blood clot formation, factors influencing blood glucose levels, glucose metabolism, factors influencing lipid metabolism, factors influencing blood cholesterol levels, factors influencing blood LDL or HDL levels, factors influencing cell apoptosis, factors influencing food intake, factors influencing energy expenditure, factors influencing appetite, factors influencing nutrient absorption, factors influencing inflammation and factors influencing bone formation. Particularly preferred are therapeutic nucleic acids encoding insulin, leptin, glucagon antagonist, GLP-1, GLP-2, Ghrelin, cholecystokinin, growth hormone, clotting factors, PYY, erythropoietin, inhibitors of inflammation, IL-10, IL-17 antagonists, TNFα antagonists, growth hormone releasing hormone, parathyroid hormone. In a preferred embodiment, the encoded therapeutic protein is insulin. In another preferred embodiment, the encoded therapeutic protein is an insulin analog. In another preferred embodiment, the encoded therapeutic protein is leptin. In another preferred embodiment, the encoded therapeutic protein is PYY.

In a preferred embodiment, the therapeutic protein is produced in a gut mucosal cell and enters the systemic circulation such that the systemic level of the therapeutic protein is increased. In a preferred embodiment, the therapeutic protein is released by regulated secretion into the systemic circulation.

In one embodiment, the systemic level of the therapeutic protein is increased by at least about 10 pM, more preferably by at least about 100 pM, more preferably by at least 1 nM, more preferably by at least about 10 nM.

In one embodiment, the systemic level of the therapeutic protein is increased by at least 10-fold, more preferably at least 100-fold, more preferably at least 125-fold, more preferably at least 150-fold, more preferably at least 200-fold, more preferably at least 200-fold, more preferably at least 500-fold, more preferably at least 750-fold, more preferably at least 1000-fold higher than the lowest detectable concentration of the therapeutic protein.

In one embodiment, the systemic level of the therapeutic protein is increased to at least 10%, more preferably 25%, more preferably 50%, more preferably, 75%, more preferably 100%, more preferably 125%, more preferably 150%, more preferably 200%, more preferably 500%, more preferably 750%, and most preferably at least 1000% of a physiologically active concentration.

In a preferred embodiment, the systemic level of the therapeutic protein is increased for longer than about 4 days, more preferably longer than about 5 days, more preferably longer than about 6 days, more preferably longer than about 7 days, more preferably longer than about 10 days, more preferably longer than about 2 weeks, more preferably longer than about 3 weeks, more preferably longer than about 4 weeks, more preferably longer than about 6 weeks, more preferably longer than about 8 weeks, more preferably longer than about 10 weeks, and most preferably longer than about 12 weeks.

In one embodiment, the increase in the systemic level of the therapeutic protein is static. In a preferred embodiment, the increase in the systemic level of the therapeutic protein is dynamic.

In one embodiment, the method comprises contacting gut mucosa in vivo with a first chitosan-based nanoparticle and a second chitosan-based nanoparticle. The first chitosan based nanoparticle is capable of transfecting a gut mucosal precursor cell in vivo and comprises (i) a plurality of chitosan polymers, and (ii) a therapeutic construct, wherein the therapeutic construct comprises a therapeutic nucleic acid operably linked to an expression control region functional in a gut mucosal cell, and an integration sequence. The second chitosan-based nanoparticle is capable of transfecting a gut mucosal precursor cell in vivo and comprises (i) a plurality of chitosan polymers, and (ii) a non-therapeutic construct, wherein the non-therapeutic construct comprises a nucleic acid encoding a means for integration operably linked to an expression control region that is functional in a gut mucosal precursor cell. A gut mucosal precursor cell in the gut mucosa is transfected with the first and second nanoparticles. The nucleic acid of the second nanoparticle is expressed in the gut mucosal precursor cell to produce a means for integration, whereby the means for integration integrates the therapeutic nucleic acid operably linked to an expression control region provided by the first nanoparticle into the genome of the gut mucosal precursor cell.

In another embodiment, the method comprises contacting gut mucosa in vivo with a chitosan-based nanoparticle comprising (i) a plurality of chitosan polymers; (ii) a therapeutic construct, wherein the therapeutic construct comprises a therapeutic nucleic acid operably linked to an expression control region functional in a gut mucosal cell, and an integration sequence; and (iii) a non-therapeutic construct, wherein the non-therapeutic construct comprises a nucleic acid encoding a means for integration operably linked to an expression control region that is functional in a gut mucosal precursor cell. A gut mucosal precursor cell in the gut mucosa is transfected using the nanoparticle. The nucleic acid encoding a means for integration is expressed in the gut mucosal precursor cell to produce a means for integration, whereby the means for integration integrates the therapeutic nucleic acid operably linked to an expression control region into the genome of the gut mucosal precursor cell.

In one aspect, the invention provides methods for increasing the systemic level of secreted therapeutic proteins in a mammal. The methods comprise contacting gut mucosa of a mammal with a chitosan-based nanoparticle of the invention, wherein the nanoparticle comprises a therapeutic nucleic acid encoding a secreted therapeutic protein, wherein the secreted therapeutic protein is produced in a mucosal cell of the gut mucosa, and wherein the secreted therapeutic protein produced in the mucosal cell enters the systemic circulation such that the systemic level of the secreted therapeutic protein is increased.

In one aspect, the invention provides methods for treating patients having diseases or conditions treatable by increasing the systemic level of therapeutic proteins. The methods comprise contacting gut mucosa of a patient with a chitosan-based nanoparticle of the invention, wherein the nanoparticle comprises a therapeutic nucleic acid encoding a secreted therapeutic protein, wherein the secreted therapeutic protein is produced in a mucosal cell of the gut mucosa of the patient, and wherein the secreted therapeutic protein produced in the mucosal cell enters the systemic circulation such that the systemic level of the secreted therapeutic protein is increased.

In a preferred embodiment, the disease is a metabolic disease.

In a preferred embodiment, the disease is diabetes mellitus.

In another preferred embodiment, the condition is morbid obesity.

In another preferred embodiment, the condition is growth deficiency.

In a preferred embodiment, the chitosan-based nanoparticle is orally administered.

In a preferred embodiment, the chitosan-based nanoparticle is administered endoscopically.

In a preferred embodiment, the chitosan-based nanoparticle is administered rectally.

In a preferred embodiment, the mucosal cell is a gut endocrine cell. In a preferred embodiment, the gut endocrine cell is selected from the group consisting of K cells, L-cells, S-cells, G-cells, D-cells, I-cells, Mo-cells, and Gr-cells. In an especially preferred embodiment, the gut endocrine cell is a K cell.

In a preferred embodiment, the mucosal cell is a mucosal cell of the small intestine. In a preferred embodiment, the mucosal cell is a mucosal cell of the duodenum, jejunum, or ileum.

In a preferred embodiment, the mucosal cell is a mucosal cell of the stomach.

In a preferred embodiment, the mucosal cell is a mucosal cell of the colon.

In a preferred embodiment, the therapeutic nucleic acid of the nanoparticle encodes a therapeutic protein that is selected from the group consisting of hormones, enzymes, cytokines, chemokines, antibodies, mitogenic factors, growth factors, differentiation factors, factors influencing angiogenesis, factors influencing blood clot formation, factors influencing blood glucose levels, factors influencing glucose metabolism, factors influencing lipid metabolism, factors influencing blood cholesterol levels, factors influencing blood LDL or HDL levels, factors influencing cell apoptosis, factors influencing food intake, factors influencing energy expenditure, factors influencing appetite, factors influencing nutrient absorption, factors influencing inflammation, and factors influencing bone formation. Particularly preferred are therapeutic nucleic acids encoding insulin, leptin, glucagon antagonist, GLP-1, GLP-2, Ghrelin, cholecystokinin, growth hormone, clotting factors, PYY, erythropoietin, inhibitors of inflammation, IL-10, IL-17 antagonists, TNFα antagonists, growth hormone releasing hormone, parathyroid hormone. In a preferred embodiment, the encoded therapeutic protein is insulin. In another preferred embodiment, the encoded therapeutic protein is an insulin analog. In another preferred embodiment, the encoded therapeutic protein is leptin. In another preferred embodiment, the encoded therapeutic protein is PYY.

In a preferred embodiment, the secreted therapeutic protein is released by regulated secretion from a gut endocrine cell.

In one embodiment, the systemic level of the therapeutic protein is increased by at least about 10 pM, more preferably by at least about 100 pM, more preferably by at least 1 nM, more preferably by at least about 10 nM.

In one embodiment, the systemic level of the therapeutic protein is increased by at least 10-fold, more preferably at least 100-fold, more preferably at least 125-fold, more preferably at least 150-fold, more preferably at least 200-fold, more preferably at least 200-fold, more preferably at least 500-fold, more preferably at least 750-fold, more preferably at least 1000-fold higher than the lowest detectable concentration of the therapeutic protein.

In one embodiment, the systemic level of the therapeutic protein is increased to at least 10%, more preferably 25%, more preferably 50%, more preferably, 75%, more preferably 100%, more preferably 125%, more preferably 150%, more preferably 200%, more preferably 500%, more preferably 750%, and most preferably at least 1000% of a physiologically active concentration.

In a preferred embodiment, the systemic level of the secreted therapeutic protein is increased for longer than about 4 days, more preferably longer than about 5 days, more preferably longer than about 6 days, more preferably longer than about 7 days, more preferably longer than about 10 days, more preferably longer than about 2 weeks, more preferably longer than about 3 weeks, more preferably longer than about 4 weeks, more preferably longer than about 6 weeks, more preferably longer than about 8 weeks, more preferably longer than about 10 weeks, and most preferably longer than about 12 weeks.

Treatment generally results in reducing or preventing the severity or symptoms of the condition in the subject, i.e., an improvement in the subject's condition or a "therapeutic effect." Therefore, treatment can reduce the severity or prevent one or more symptoms of the condition or an associated disorder, inhibit progression or worsening of the condition or an associated disorder, and in some instances, reverse the condition or an associated disorder. Thus, in the case of a hyperglycemic condition, for example, treatment can reduce blood glucose, improve glucose tolerance, provide normal glucose homeostasis, or prevent, improve, or reverse a histopathological change associated with or that results from the hyperglycemic condition.

Improvement of a histopathological change associated with a hyperglycemic condition includes, for example, preventing further or reducing kidney tubule calcification, decreasing or arresting retinopathy or cataracts, decreasing wound or injury healing time, reducing diabetic foot, preventing or reducing accelerated periodontitis, or decreasing the risk of developing coronary heart disease, stroke, peripheral vascular disease, dyslipidemia, hypertension and obesity. Improvement in obesity can include, for example, a reduction of body mass or an improvement in an associated disorder, such as a decrease in cholesterol, LDL or VLDL levels, a decrease in blood pressure, a decrease in intimal thickening of the blood vessel associated with high fat diet, a decrease in resting heart rate, an increase in lung capacity, etc. Improvement in a bleeding disorder, such as hemophilia can induce, for example, decreased clotting time or frequency/duration of bleeding episodes.

As used herein, the term "ameliorate" means an improvement in the subject's condition, a reduction in the severity of the condition, or an inhibition of progression or worsening of the condition. In the case of a hyperglycemic condition (e.g., diabetes), for example, an improvement can be a decrease in blood glucose, an increase in insulin, an improvement in glucose tolerance, or glucose homeostasis. An improvement in a hyperglycemic condition also can include improved pancreatic function (e.g., inhibit or prevent β-islet cell destruction), a decrease in a pathology associated with or resulting from the condition, such as an improvement in histopathology of an affected tissue or organ, as set forth herein. In the case of obesity, for example, an improvement can be a decrease in weight gain, a reduction of body mass or an improvement in a conditions associated with obesity, as set forth herein (e.g., reduction of blood glucose, cholesterol, LDL or VLDL levels, a decrease in blood pressure, a decrease in intimal thickening of the blood vessel, etc.). In the case of hemophilia or other blood coagulation/clotting/bleeding disorders, an improvement can reduce the frequency or duration of bleeding episodes or hemorrhage. Improvements likewise include chronic disorders associated with blood coagulation/clotting/bleeding associated disorders such as a reduction in neurological problems, crippling tissue and joint damage, for example.

The methods of the invention for treating a subject are applicable for prophylaxis to prevent a condition in a subject, such as a hyperglycemic condition or an associated disorder, or development of obesity or an increased body mass. Alternatively, the methods can be practiced following treatment of a subject as described herein. For example, following treatment and a reduction of body mass to the desired weight, leptin, GLP-1, PYY or CCK can be periodically produced by gut mucosal cells, as described herein, in order to suppress appetite, decrease meal consumption, etc. thereby maintaining desired body weight.

The methods of the invention for treating a subject also can be supplemented with other forms of therapy. Supplementary therapies include drug treatment, a change in diet (low sugar, fats, etc.) surgical resection, transplantation, radiotherapy, etc. For example, a method of the invention for treating a hyperglycemic condition can be used in combination with drugs or other pharmaceutical formulations that increase insulin or lower glucose in a subject. Drugs for treating diabetes include, for example, biguanides and sulphonylureas (e.g., tolbutamide, chlorpropamide, acetohexamide, tolazamide, glibenclamide and glipizide). Appetite suppression drugs are also well known and can be used in combination with the methods of the invention. Supplementary therapies can be administered prior to, contemporaneously with or following the invention methods of treatment. The skilled artisan can readily ascertain therapies that may be used in a regimen in combination with the treatment methods of the invention.

Pharmaceutical Formulations

As the methods of the invention can include contacting a mucosal cell(s) present in a subject with a polynucleotide, the present invention also provides "pharmaceutically acceptable" or "physiologically acceptable" formulations comprising chitosan-based nanoparticles of the invention. Such formulations can be administered in vivo to a subject in order to practice the treatment methods of the invention.

As used herein, the terms "pharmaceutically acceptable" and "physiologically acceptable" refer to carriers, diluents, excipients and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

A pharmaceutical formulation can be formulated to be compatible with its intended route of administration. The preferred route of administration in the present invention is oral, endoscopic, or rectal. Thus, preferred pharmaceutical formulations include carriers, diluents, or excipients suitable for administration by routes including oral, endoscopic and rectal, though other formulations and other routes of administration capable of reaching the gut lumen, especially of the stomach, small intestine, and colon are contemplated.

For oral administration, a composition can be incorporated with excipients and used in the form of tablets, troches, or capsules, e.g., gelatin capsules. Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or flavoring.

Formulations can also include carriers to protect the composition against rapid degradation or elimination from the body, such as a controlled release formulation, including implants and microencapsulated delivery systems. For example, a time delay material such as glyceryl monostearate or glyceryl stearate alone, or in combination with a wax, may be employed.

Suppositories and other rectally administrable formulations (e.g., those administrable by enema) are also contemplated. Further regarding rectal delivery, see, for example, Song et al., *Mucosal drug delivery: membranes, methodologies, and applications*, Crit. Rev. Ther. Drug. Carrier Syst., 21:195-256, 2004; Wearley, Recent progress in protein and peptide delivery by noninvasive routes, Crit. Rev. Ther. Drug. Carrier Syst., 8:331-394, 1991.

Additional pharmaceutical formulations appropriate for administration are known in the art and are applicable in the methods and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; and Pharmaceutical Principles of Solid Dosage Forms, Technonic Publishing Co., Inc., Lancaster, Pa., (1993)).

Administration

A preferred route of administration is oral. For oral administration, a composition can be incorporated with excipients and used in the form of tablets, troches, or capsules, e.g., gelatin capsules. Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or flavoring.

Endoscopes, cannulas, intubation tubes, catheters and the like can be used to deliver the formulation to various parts of the gut of a subject. This allows effective delivery and targeting of nanoparticles to particular areas of the gut. In one aspect, the invention provides delivery devices comprising a chitosan-based nanoparticle composition disclosed herein.

The doses or "effective amount" for treating a subject are preferably sufficient to ameliorate one, several or all of the symptoms of the condition, to a measurable or detectable extent, although preventing or inhibiting a progression or worsening of the disorder or condition, or a symptom, is a satisfactory outcome. Thus, in the case of a condition or disorder treatable by expressing a therapeutic nucleic acid in gut mucosal cells, the amount of therapeutic RNA or therapeutic protein produced to ameliorate a condition treatable by a method of the invention will depend on the condition and the desired outcome and can be readily ascertained by the skilled artisan. Appropriate amounts will depend upon the condition treated, the therapeutic effect desired, as well as the individual subject (e.g., the bioavailability within the subject, gender, age, etc.).

Veterinary applications are also contemplated by the present invention. Accordingly, in one embodiment, the invention provides methods of treating non-human mammals, which involve administering a chitosan-based nanoparticle of the invention to a non-human mammal in need of treatment.

The effective amount can be ascertained by measuring relevant physiological effects. For example, in the case of diabetes or other hyperglycemic condition, a decrease in blood glucose or an improvement in glucose tolerance test can be used to determine whether the amount of insulin is effective to treat the hyperglycemic condition. For example, an amount reducing FPG from 126 mg/dl to 120, 115, 110, or less is an effective amount. In the case of obesity or an undesirable body mass, a decrease in the subjects' mass, a decrease in meal size or caloric content of a meal, increased satiety for a given meal size, and decreases in serum/plasma levels of lipid, cholesterol, fatty acids, LDL or VLDL all can be effective amounts for ameliorating obesity or an undesirable body mass of a subject. In the case of hemophilia, an effective amount is an amount which reduces clotting time or frequency or duration of bleeding episodes in a subject.

The mucous of the mucosal tissue may be removed or otherwise prepared prior to administration, for example, using penetrants or other barrier penetration enhancers. Such penetrants appropriate to the barrier to be permeated are generally known in the art, and include, for example, for transmucosal administration, incubation with N-acetyl-cysteine (Nakanishi et al. Chem Pharm Bull (Tokyo) 40:1252 (1992), Meaney and O'Driscoll Eur J Pharm Sci. 8:167 (1999); hydrolysis of intestinal mucins by purified Sigma 1 protein and infectious subviral particles (Bisaillon et al. J Mol. Biol. 286:759 (1999); removal of mucous and increase in gene transfer by Dodecyl β-D-maltoside Connor et al, Gene Ther. 2001 January; 8(1):41-8; desialation (Slomiany et al. Gen Pharmacol. 27:761 (1996); (Hirmo et al. FEMS Immunol Med. Microbiol. 20:275 (1998); desulphation by *H. pylori* glycosulfatase (Slomiany et al. Am J GastroenteroL 87:1132 (1992); desialation by neuraminidase (Hanski et al. Cancer Res. 51:5342 (1991)); disulphide bond breakage by β-mercaptoethanol (Gwozdzinski et al. Biochem Int. 17:907 (1988); deglycosylation with specific exoglycosidases such as fucosidase, β-galactosidase, N-acetyl-galactosaminidase, β-N-acetyl hexososaminidase, and neuraminidase (Slomiany et al. Biochem Biophys Res Commun. 142:783 (1987); acid removal of by 0.4 N HCl (Ruggieri et al. Urol Res. 12:199 (1984), Davis C. P. and Avots-Avotins A. E. Scan Electron Microsc. (Pt 2):825-30 (1982), Parsons et. al. Am J. Pathol. 93:423 (1978)), among others.

The number of precursor cells in the gut mucosa can be increased by exposure to cytotoxic agents and growth factors. For example, irradiation of the small gut increases the number clonogenic/stem cells (Roberts S. A. Radiat. Res. 141:303 (1995); Cai W. B. et. al. Intl. J. Radiat. Biol. 71:145 (1997)). In addition, treatment with GLP-2, epidermal growth factor, TGF-α, insulin-like growth factors, interleukins, among others, have been shown to promote the growth of mucosal cells (Potten C. S. Int. J. Exp. Path 78:219 (1997)). In this way, additional target cells can be produced thereby increasing transfection efficiency and subsequent regulated protein production by modified gut mucosal cells.

Physicochemical Properties of Various Chitosan/DNA Polyplexes

Table 4 shows physiochemical properties of exemplary chitosan-based nanoparticles.

| Chitosan | Avg. No. Monomers based on Avg. Weight | mol. wt kDa | DDA (%) | N:P ratio | Particle size (nm) | Zeta potential (mV) |
|---|---|---|---|---|---|---|
| P3; C(15, 98) | 15 | 2.4 | 98 | 60 | 140 | +34.8 |
| P1; C(24, 98) | 24 | 3.9 | 98 | 60 | 123 | +37.9 |
| RC05; C(1199, 74) | 1199 | 206 | 74 | 2.9 | 205 | +6.2 |
| CH01; C(2038, 95) | 2038 | 332 | 95 | 3.82 | 243 | +8.5 |
| CH10; C(2036, 83) | 2036 | 342 | 83 | 3.24 | 243 | +6.5 |

Size was measured at 30 minutes and zeta potential was measured at 5 hours, each composition having a DNA concentration of 50 μg/ml, and a pH of 5.5 (RC05, CH01, CH10) or 5.0 (P1 and P3). Using the "C" nomenclature for chitosan, the first factor refers to the average number of monomers, and the second factor refers to the DDA.

As DNA concentration is varied in compositions composed of chitosan polymers having the same or similar average molecular weight, the N:P ratio is preferably varied for optimization. For example, for compositions comprising chitosan-based nanoparticles composed of chitosan polymers having an average molecular weight of about 3.9 kDa and a DDA of about 98% (P1 above), and a DNA concentration of about 50 μg/ml, a highly preferred N:P ratio is 60:1. For a composition comprising the same chitosan-based nanoparticles composed of chitosan polymers having an average molecular weight of about 3.9 kDa and a DDA of about 98%, but a DNA concentration of about 250 μg/ml, a more highly preferred N:P ratio is 20:1. In general, as the DNA concentration is increased, it is preferable to decrease the N:P ratio, especially for low molecular weight chitosan nanoparticles.

At pHs below the pKa of the amine group of chitosan, the N:P ratio more closely reflects the actual charge ratio in the nanoparticle. In a preferred embodiment, the compositions of the invention have a pH of less than 6.5, more preferably less than 6.0, and most preferably between about 4.5 and about 5.5, and N:P ratio very closely reflects actual charge ratio.

Notably, zeta potential varies with pH and the extent of protonation of chitosan amine groups. Generally, as the pH increases and the extent of protonation of chitosan amine groups decreases, the zeta potential decreases.

Also, as the degree of acetylation (DDA) is varied for chitosan polymers having the same average monomer length, it is preferable to adjust the N:P ratio in compositions. For example, for compositions comprising chitosan-based nanoparticles having an average monomer length of about 24, a DDA of about 98%, and a DNA concentration of about 250 µg/ml, a highly preferred N:P ratio is 20:1. For a composition comprising the same chitosan-based nanoparticles having an average monomer length of about 24, a DNA concentration of about 250 µg/ml, but a DDA of about 80%, a highly preferred N:P ratio is 40:1. In general, as the DDA is decreased, it is preferable to increase the N:P ratio, especially for low molecular weight chitosan nanoparticles.

All citations are expressly incorporated herein in their entirety by reference.

EXPERIMENTAL

Formation of Chitosan-Based Nanoparticles (compositions relating to data FIGS. 1-10) Plasmid DNA and chitosan solutions, prepared separately, were adjusted to a concentration equal to two-times the required final concentration. For P3 and P1, DNA was diluted in water and the indicated chitosan was dissolved in 5 mM sodium acetate, pH5.0. For other complexes in Table 5, DNA was diluted in 50 mM sodium sulfate solution, and the indicated chitosan was dissolved in 5 mM sodium acetate, pH5.5. In all cases, both solutions were incubated at 55° C. for 5 minutes before being mixing. Equal volumes of the two solutions were mixed and rapidly vortexed for 30 seconds to form DNA/chitosan particles. For certain applications, this preparation was further diluted in various buffers prior to analysis. Chitosan used was obtained from FMC (Norway) and Biosyntech (Canada).

TABLE 5

Chitosan-based Nanoparticle Formulations

| Polymer | avg # monomer units | % Deacetylation | N:P ratios tested | W:W ratios (chi:DNA) | DNA Concentration tested (ug/ml) |
|---|---|---|---|---|---|
| P3 | 15 | 98 | 60 | 31 | 50 |
| | | | 50 | 26 | 50 |
| | | | 40 | 21 | 50 |
| | | | 30 | 15.5 | 50 |
| | | | 15 | 7.8 | 50 |
| | | | 7.5 | 3.9 | 50 |
| | | | 3.75 | 1.9 | 50 |
| | | | 2 | 1 | 50 |
| | | | 1 | 0.5 | 50 |
| P1 | 24 | 98 | 120 | 60 | 50 |
| | | | 80 | 40 | 50 |
| | | | 60 | 30 | 50 |
| | | | 50 | 25 | 50 |
| | | | 40 | 20 | 50 |
| | | | 30 | 15 | 50 |
| | | | 25 | 12.5 | 50 |
| | | | 20 | 10 | 50 |
| | | | 15 | 7.5 | 50 |
| | | | 10 | 5 | 50 |
| | | | 7.5 | 3.75 | 50 |
| | | | 3.75 | 1.875 | 50 |
| | | | 2 | 1 | 50 |
| | | | 1 | 0.5 | 50 |
| AS-111-39-A | 98 | 84 | 30 | 18.5 | 50 |
| | | | 15 | 9.25 | 50 |
| | | | 7.5 | 1.23 | 50 |
| | | | 1 | 0.62 | 50 |
| AS-111-39-B | 260 | 84 | 20 | 12.3 | 50 |
| | | | 10 | 6.2 | 50 |
| | | | 5 | 3.1 | 50 |
| | | | 1 | 0.62 | 50 |
| UPC113 | 677 | 86 | 3.40 | 2 | 50 |
| RC05 | 1199 | 74 | 5.7 | 4 | 25, 50 |
| | | | 2.85 | 2 | 50, 200 |
| | | | 1.90 | 1.33 | 75 |
| | | | 1.42 | 1 | 50, 100 |
| | | | 0.95 | 0.665 | 150 |
| | | | 0.71 | 0.5 | 200 |
| CH01 | 2038 | 95 | 3.82 | 2 | 50 |
| | | | 1.91 | 1 | 100 |
| | | | 0.96 | 0.5 | 200 |
| | | | 0.38 | 0.2 | 500 |
| CH10 | 2036 | 83 | 3.24 | 2 | 50, 200 |
| | | | 1.62 | 1 | 100 |
| | | | 0.33 | 0.2 | 500 |

Transfection of 293T Cells Using Chitosan-Based Nanoparticles

Human embryonic kidney cells carrying the SV40 large-T antigen (293T) were grown in Dulbecco's Modified Eagle Medium (DMEM) supplemented with 10% fetal calf serum. They were trypsinized, washed in PBS and plated in complete medium at approximately $6 \times 10^5$ cells in 3 ml of media per well of a 6-well plate. For DNA/chitosan-mediated transfection, cells were washed the following day with serum free Optimem prior to addition of the DNA/chitosan particles. The medium used for these incubations was either serum-free Optimem, pH 7.4 or Optimem adjusted to pH 5.0. 4 hours after transfection, 3 ml of Optimem, pH 7.4 was added to each well. Forty-eight hours after transfection with a β-galactosidase plasmid under control of the CMV promoter (pShuttle-CMV-LacZ), cells were assayed for β-galactosidase activity using the Galacto-Light Plus System (ABI). Briefly, cells were washed twice with PBS, lysed with 200 µl lysis buffer containing protease inhibitor and detached with a cell scraper. Cell lysate was clarified by spinning at maximum speed for 2 min and 20 ml was assayed according to manufacturer's instructions. Signal was detected using the LMax II384 luminometer (Molecular Devices) with a 1 sec integration. The β-galactosidase activity was corrected for total protein in the sample by measuring protein content using the Bio-Rad DC Protein assay according to the manufacturer's instructions.

Nanoparticle Formation Analysis

The ability of chitosan to complex and retain its interaction with DNA was assessed by gel electrophoresis in 0.8% agarose in 0.04M Tris, 0.001M sodium acetate, 0.02M EDTA buffer, pH 8 (TAE) with ethidium bromide (0.2 µg/ml). Gels were run at 100 mV for 1 h and DNA retention was visualized under UV light. (data not shown)

Viral Vectors

Gene transfer vectors based on feline immunodeficiency virus (FIV) and adeno-associated virus (AAV) carrying marker genes of interest (e.g. insulin, β-galactosidase or SEAP) were produced. FIV vector was generated using standard methods. AAV2 particles carrying transgenes of interest were also generated using standard methods. Particles were harvested by using a HiTrap Heparin HP column (Amersham) three days following transfection.

Gene Transfer to the Duodenum In Vivo

Chitosans CH01 (N:P 3.82), CH10 (N:P 3.24), RC05 (N:P 2.85), P1 (N:P 60) and P3 (N:P 60) were used to form complexes with 12.5 µg plasmid DNA (50 µg/ml), as described above, prior to administration to mice (FIG. 2). Additional experiments using P1 and RC05 used a range of N:P ratios as described in FIG. 3. Briefly, an abdominal incision was made in anaesthetized and overnight-fasted mice. A section of the duodenum (2 cm from the pyloric sphincter) was isolated and externalized with an immobilized glass hook. The lumen of the duodenal section was washed once with saline and optionally incubated with a mucolytic agent (10% NAC) for 10 minutes. Following the incubation, the mucolytic agent was pushed to the distal region of the intestinal tract and washed thrice with saline. Two hundred microliters of the gene transfer solution (chitosan-based nanoparticle preparation, or comparative viral vector) was then delivered into the lumen of the isolated duodenal section and incubated for 1 hour with the duodenal section stabilized with a glass hook in an elevated position. The externalized gut section was covered in a saline-soaked gauze to prevent excessive tissue drying. Following incubation, the duodenal section was returned to the abdomen and the incision was closed with 5-0 vicryl suture. Each mouse was administered 100 mg/kg ampicillin (i.p.), 5 mg/kg ketaprofen (s.c.) and 1 ml lactated ringers solution (s.c.) upon completion of the surgery. Animals were then ear marked and returned to their cages to recover on heating pads.

For oral administration of DNA/chitosan complexes, 500 µl of test solution was administered to the stomach of mice using a gavage needle.

Quantitative PCR to Measure Gene Delivery to the Duodenum

The amount of DNA transfected into duodenal tissue was measured by quantitative polymerase chain reaction (Q-PCR). Tissue samples were thawed to room temperature then ground with a pestle and mortar. DNA was extracted using the manufacturer's instructions for the Qiagen DNeasy Tissue Kit, except that double the listed volumes of proteinase K and ATL buffers were used. Genomic DNA concentrations were measured using a spectrophotometer prior to amplification using primers specific for the particular transgene being tested. Standardization was also carried out using primers for 18S RNA coding sequence. The amplification was quantified using blank samples spiked with plasmid DNA. Amplification was carried out using and ABI 7000 cycler.

Long-Term Increase in Systemic Protein Following Transfection of Gut Mucosal Cells The ability to generate long-term expression was assessed in the small intestine of mice. The SEAP plasmid complexed with chitosan was applied to the duodenum as described above. The plasmid contained the SEAP gene under the control of the constitutive promoter EF1α. The plasmid also contained a bacterial origin of replication and an ampicillin selectable marker.rGIP-hINS.

Integration of Therapeutic Nucleic Acid

Figure 6:
FIG. 6 shows results of in vivo transfection (single administration) of murine gut mucosal cells of the duodenum with P1 chitosan-based nanoparticles at an N:P ratio of 60:1 wherein the nanoparticles comprise (i) CMV-lacZ integration construct (pMM2611-beta-gal), and (ii) CMV-Mariner expression construct (pCMV-C9.gck). Gene copy number at 14 days post transfection is shown.

Chitosan P1 (N:P 60) used to form complexes with a total of 12.5 µg plasmid DNA (50 µg/ml) prior to administration to mice, as described above. Reporter gene integration plasmid contains an origin of replication, an ampicillin resistance gene and a CMV promoter driving the expression of the beta-galactosidase reporter gene (pMM2611). The reporter cassette is flanked on either side by inverted terminal repeats (ITRs) which are recognized and integrated into the host genome by the mariner transposase. The mariner transposase itself was delivered on the pCMV-9 plasmid, driven by the CMV promoter, which also contains an origin of replication and an ampicillin resistance gene used for selection during bacterial propagation. See FIG. 7 for plasmid maps. The plasmids were mixed at a 5:1 (pMM2611:pCMV-C9) prior to complexation with chitosan. FIG. 6 shows cotransfection of mouse duodenum cells in vivo with chitosan-based nanoparticles P1 at a NP ratio of 60:1.

Measurement of SEAP Activity In Vivo

SEAP levels in mouse plasma were determined using the Roche chemiluminescent SEAP Reporter Gene Assay. Frozen samples were thawed, vortexed, spun down, diluted and heat inactivated at 69° C. for 45 min. After heat inactivation, samples were cooled on ice, centrifuged and assayed according to manufacturer's instructions. Signal was detected using the LMax II384 luminometer (Molecular Devices) with a 1 sec integration.

Results: FIG. 1 shows results of in vitro transfection of 293 cells with chitosan-based nanoparticles comprising chitosan polymers of various molecular weights and degrees of deacetylation (see Table 4 for details). Chitosans CH01 (N:P 7.6), CH10 (N:P 6.5), RC05 (N:P 5.7), P1 (N:P 60) and P3 (N:P 60) were complexed with the pShuttle-CMV-LacZ plasmid prior to transfection and β-galactosidase activity was measured as a measure of transfection efficiency. These results show differences in transfection efficiency depending on the particular chitosan used and very significant levels of transfection relative to naked DNA.

Figure 2:
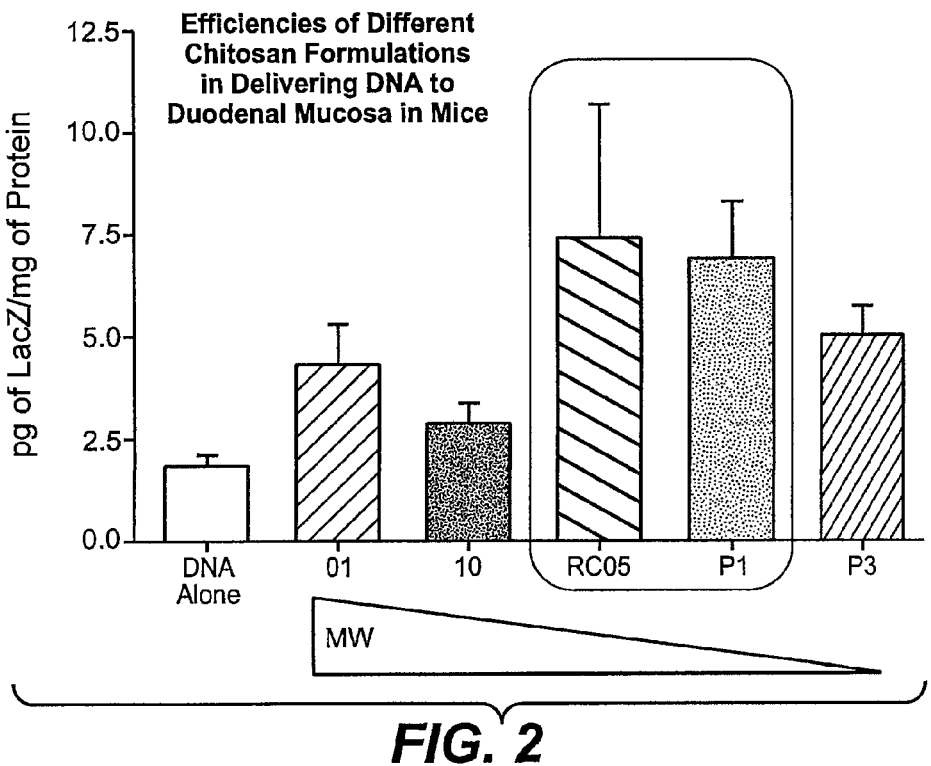
FIG. 2 shows results of in vivo transfection of murine gut mucosal cells of the duodenum with chitosan-based nanoparticles comprising chitosan polymers of various molecular weights, as indicated.

FIG. 2 shows results of in vivo transfection of murine luminal cells of the duodenum with chitosan-based nanoparticles comprising chitosan polymers of various molecular weights and degrees of deacetylation (see Table 4 for details). Chitosans CH01 (N:P 3.82), CH10 (N:P 3.24), RC05 (N:P 2.85), P1 (N:P 60) and P3 (N:P 60) were complexed with the pShuttle-CMV-LacZ plasmid prior to transfection, and β-galactosidase activity was measured as a measure of transfection efficiency. These results show differences in transfection efficiency depending on the particular chitosan used. RC05 also gives a clear illustration of differences between the transfection efficiency obtained in vitro and in vivo.

Figure 3:
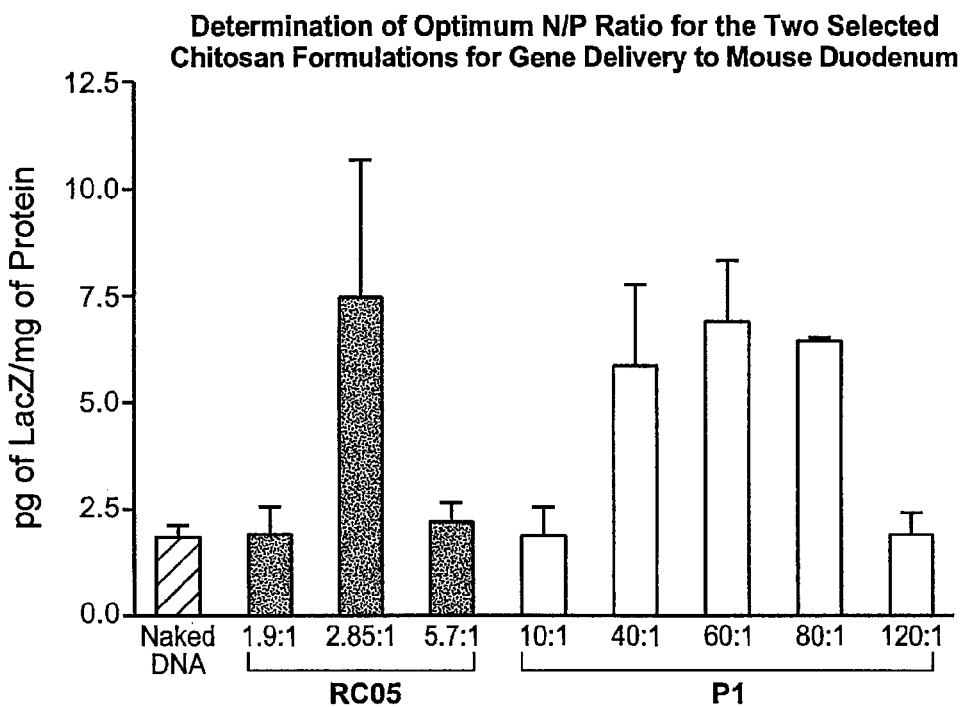
FIG. 3 shows results of in vivo transfection of murine gut mucosal cells of the duodenum with chitosan-based nanoparticles comprising chitosan polymers of various molecular weights and at various N:P ratios, as indicated.

FIG. 3 shows results of in vivo transfection of murine luminal cells of the duodenum with chitosan-based nanoparticles comprising chitosan polymers of various molecular weights (see Table 4 for details) and at various N:P ratios, as indicated. The pShuttle-CMV-LacZ plasmid was used for transfection, and β-galactosidase activity was measured as a measure of transfection efficiency. These results show differences in transfection efficiency depending on the NP ratio used and that the optimal NP ratio is different for various chitosan molecules.

Figure 4:
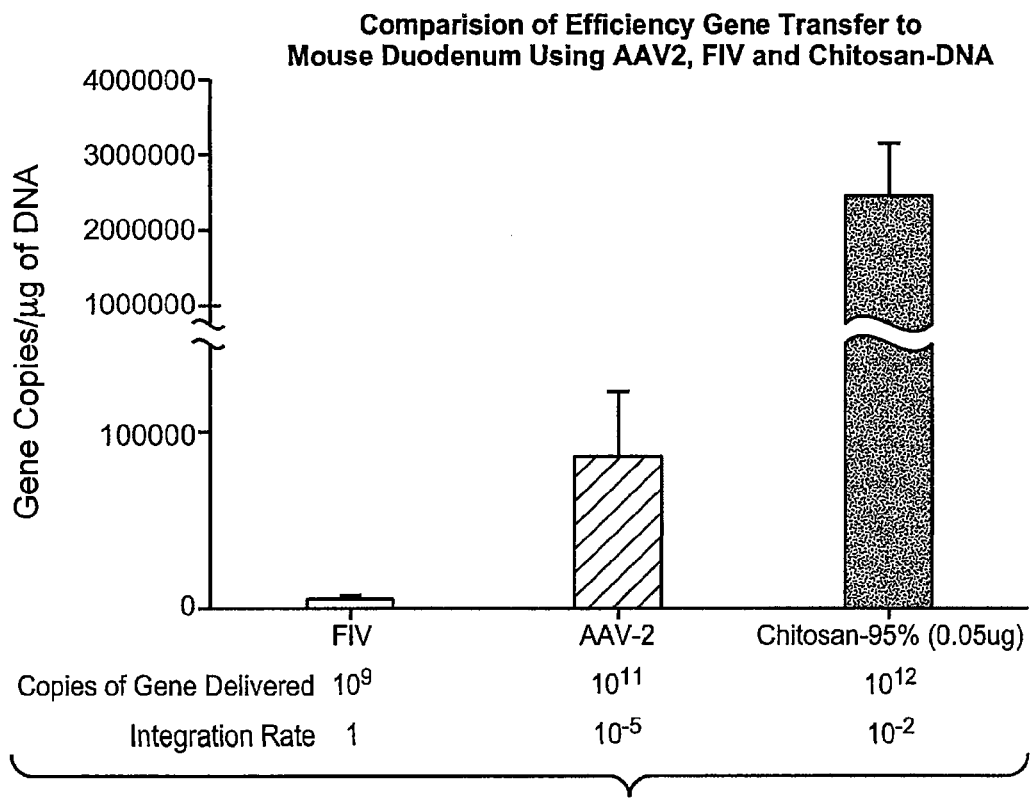
FIG. 4 shows results of in vivo transfection of murine gut mucosal cells of the duodenum with RCO5 chitosan-based nanoparticles at an N:P ratio of 2.85:1, compared to transduction with FIV and AAV particles.

FIG. 4 shows results of in vivo transfection of murine luminal cells of the duodenum with RC05 chitosan-based nanoparticles at an N:P ratio of 2.85:1, compared to transduction with FIV (109 transduction units) and AAV (1011 transduction units) particles. Data represent the number of gene copies detected in the tissue using quantitative PCR. This data shows that chitosan-mediated gene transfer to the gut using particular formulations is more effective than what are normally considered effective viral gene transfer systems.

Figure 5:
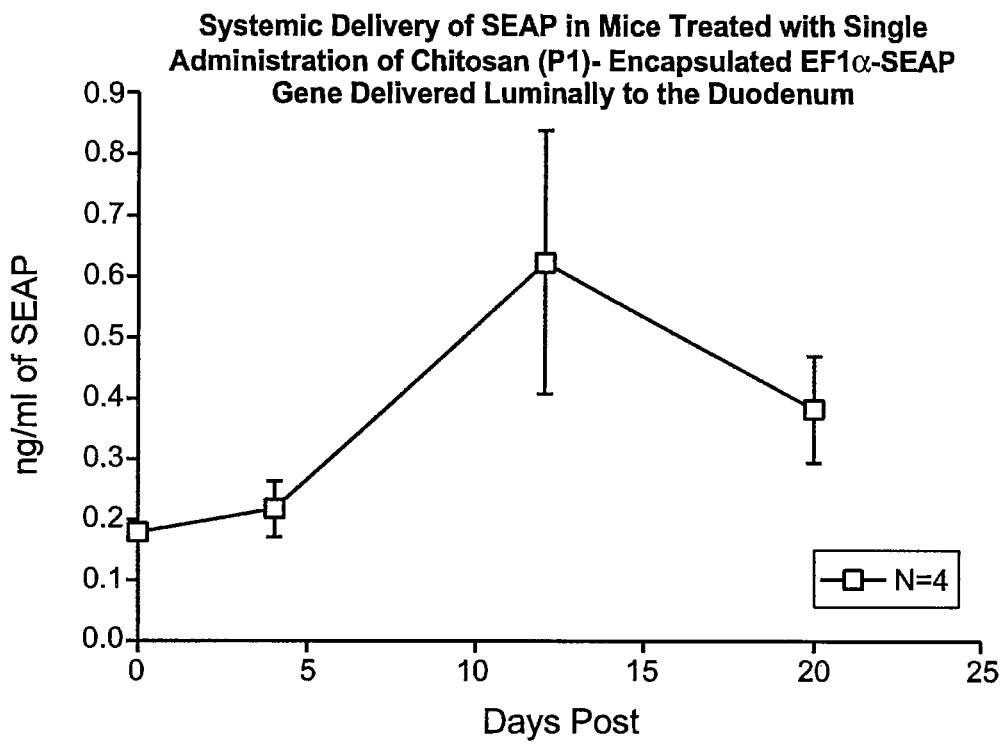
FIG. 5 shows results of in vivo transfection (single administration) of murine gut mucosal cells of the duodenum with P1 chitosan-based nanoparticles at an N:P ratio of 60:1, wherein the nanoparticle comprises an EF1α-SEAP construct. The level of SEAP protein in blood at various time points is shown.

FIG. 5 shows results of in vivo transfection (single administration) of murine luminal cells of the duodenum with P1 chitosan-based nanoparticles at an N:P ratio of 60:1, wherein the nanoparticle comprises an EF1a-SEAP plasmid. The level of SEAP protein in blood at various time points is shown. This data illustrates the ability of chitosan to deliver long-term gene expression in the duodenum of mice.

FIG. 6 results of in vivo transfection and effect of integration in murine luminal cells of the duodenum with P1 chitosan-based nanoparticles at an N:P ratio of 60:1. Two plasmids (pMM2611-beta-gal containing one ITR on either side of the LacZ gene; pCMV-C9 encoding the Mariner integrase) were mixed at a ratio of 5:1 prior to complexation with P1 chitosan. Duodenum was harvested 14 days following transfection and the presence of pMM2611-beta-gal plasmid was measured by quantitative PCR.

Figure 7A:
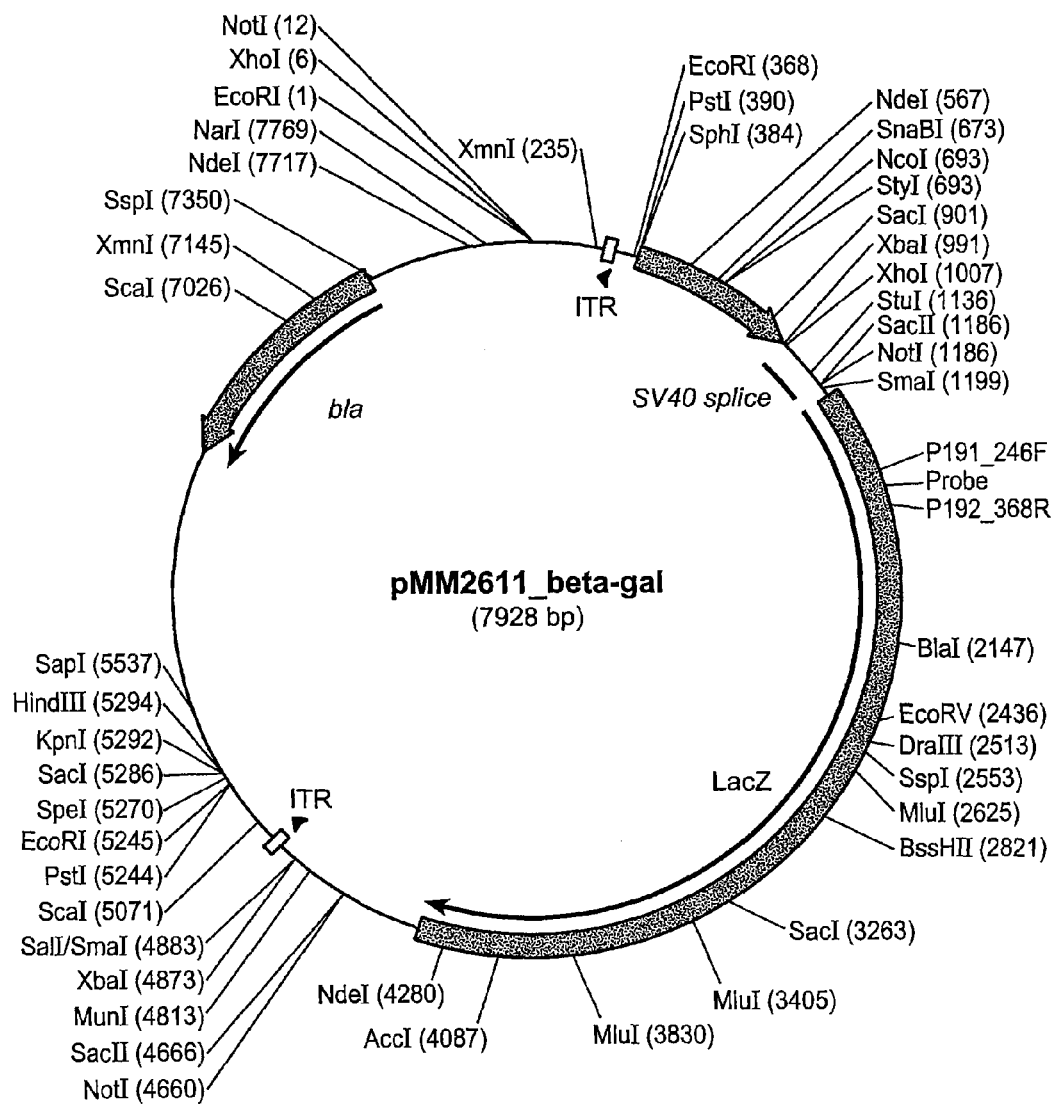
FIG. 7A shows schematic of CMV-lacZ integration construct (pMM2611-beta-gal) used with Mariner transposase.
Figure 7B:
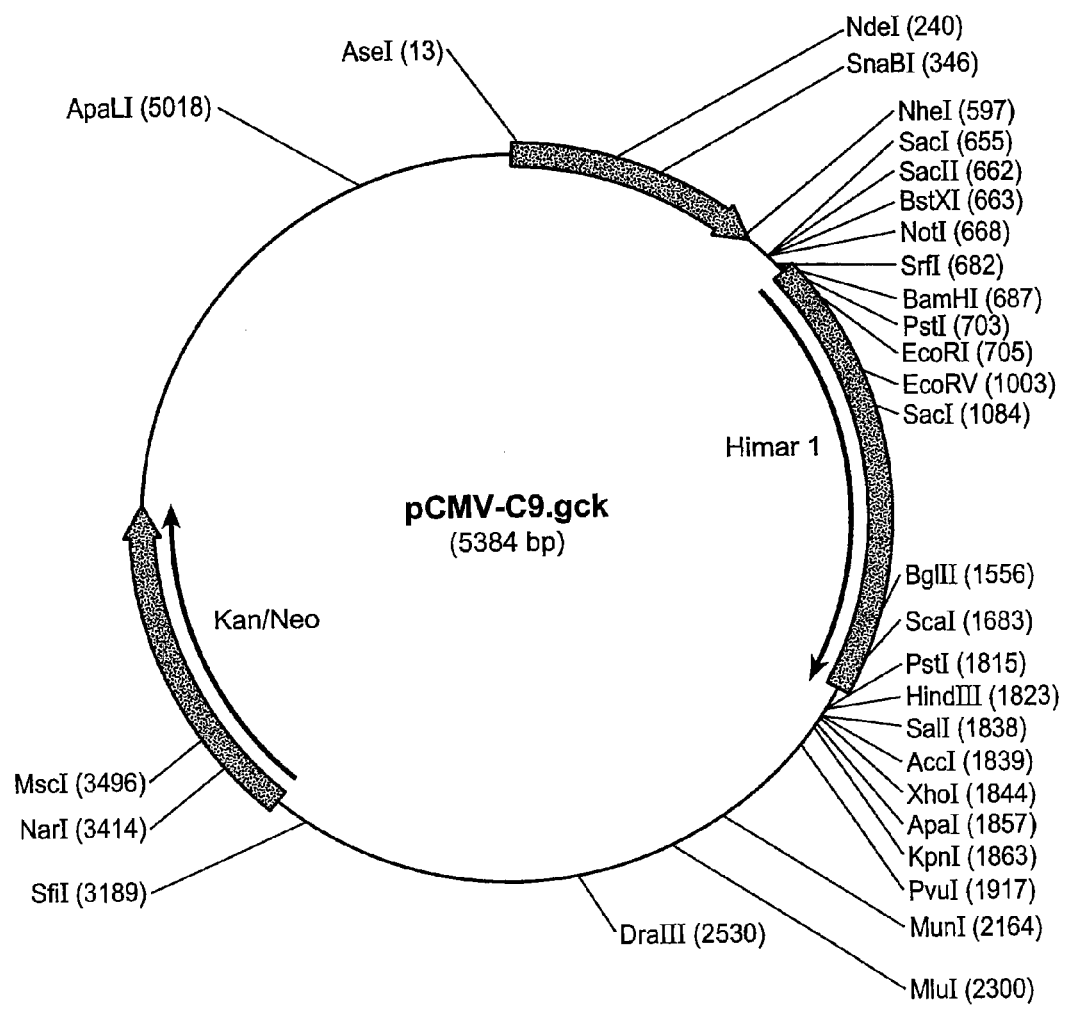
FIG. 7B shows schematic of Mariner expression construct (pCMV-C9.gck).

FIG. 7 shows two schematics of the plasmids, pCMV-C9 (Panel A) and pMM2611-beta-gal (Panel B), used in the experiment shown in FIG. 6. The diagrams show the main sequence elements such as promoters, transgenes and ITR integration sites. The principal restriction enzyme sites are also shown.

Chitosan Mediated Gene Transfer to Duodenal Mucosal Cells in Mice at 2 Days Post Delivery, and Persistence at 14 Days Post Delivery with Use of ΦC31

Q-PCR on mouse duodenum after gene transfer with chitosan-DNA nanoparticles: To quantitate gene copy number after luminal delivery of chitosan-DNA nanoparticles to the duodenum of mice, mouse duodenum was collected 2 or 14 days post polyplex delivery and the DNA was extracted using the Qiagen DNeasy. Tissue Kit. Real-time quantitative PCR (Q-PCR) was subsequently performed on 1 μg of DNA with TaqMan PCR Master Mix (Applied Biosystems) and primers and probes specific to either the LacZ or luciferase gene. Q-PCR using 18S primers and probe (Applied Biosystems) was performed as an internal control.

Figure 8A:
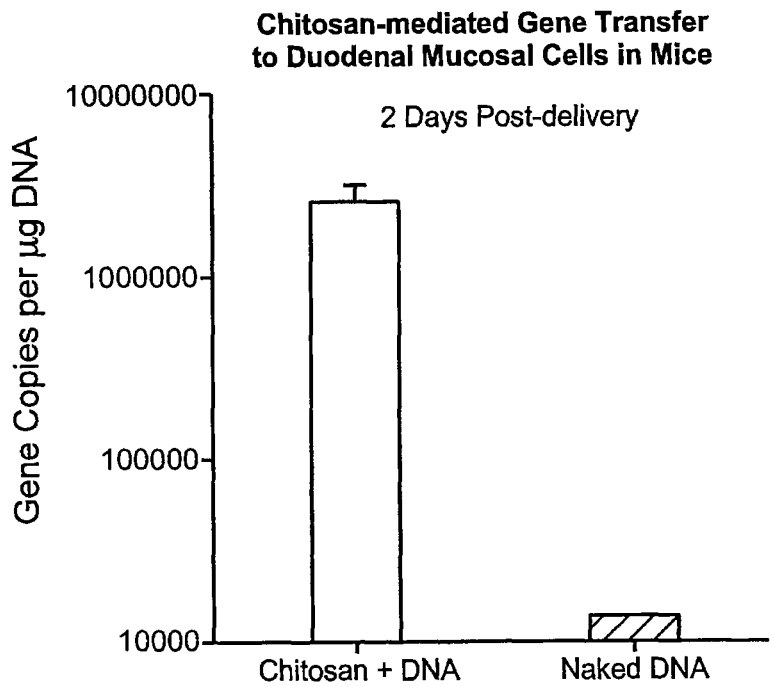
FIG. 8 shows results of chitosan mediated gene transfer to duodenal mucosal cells in mice at 2 days post delivery, and persistence at 14 days post delivery with use of ΦC31
Figure 8B:
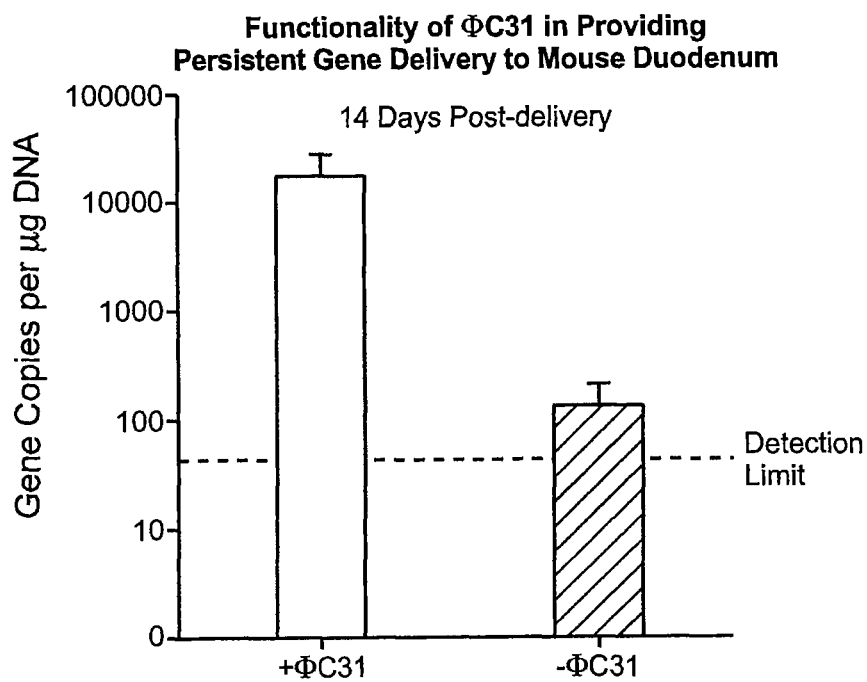
Figure 9:
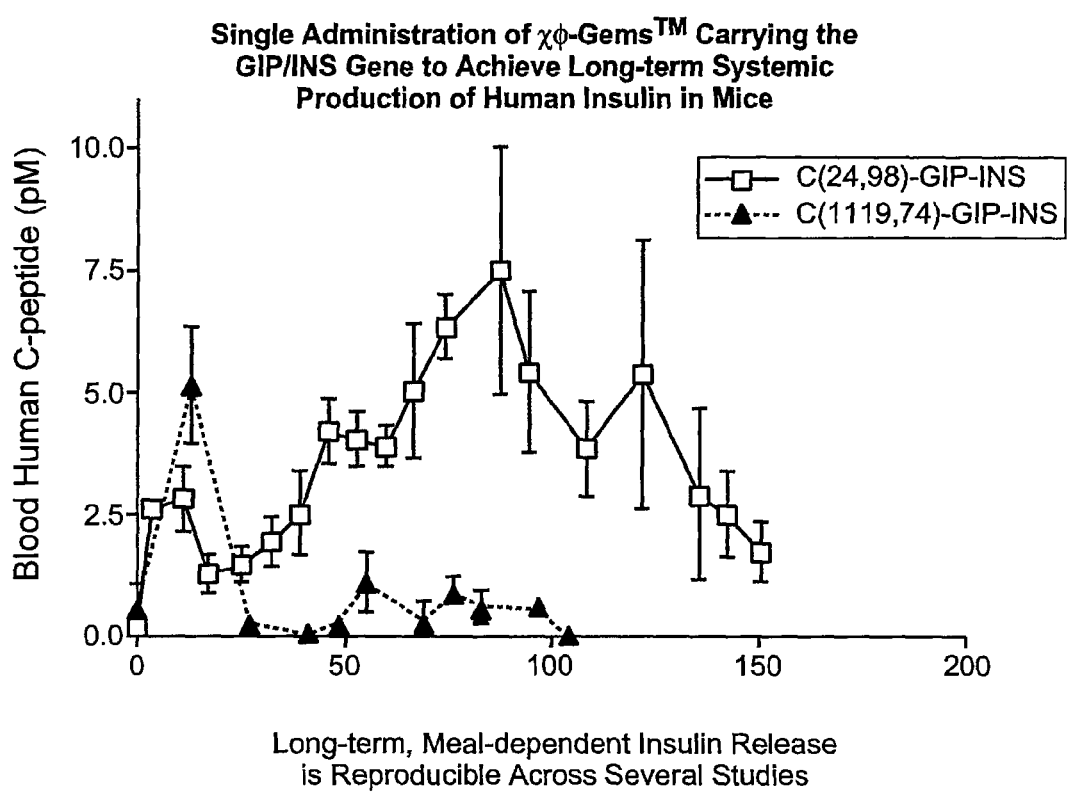
FIG. 9 shows results of single administration of χΦ-GEMST™ carrying the GIP-hINS gene to achieve long-term systemic production of human insulin in mice.
Figure 10:
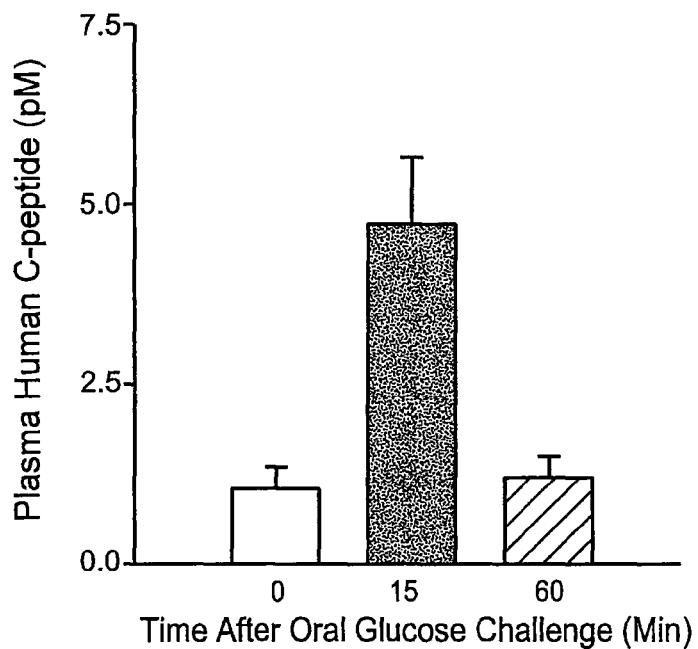
FIG. 10 shows results of glucose and meal challenge in mice treated with chitosan-based nanoparticle carrying GIP-insulin gene.
Figure 10:
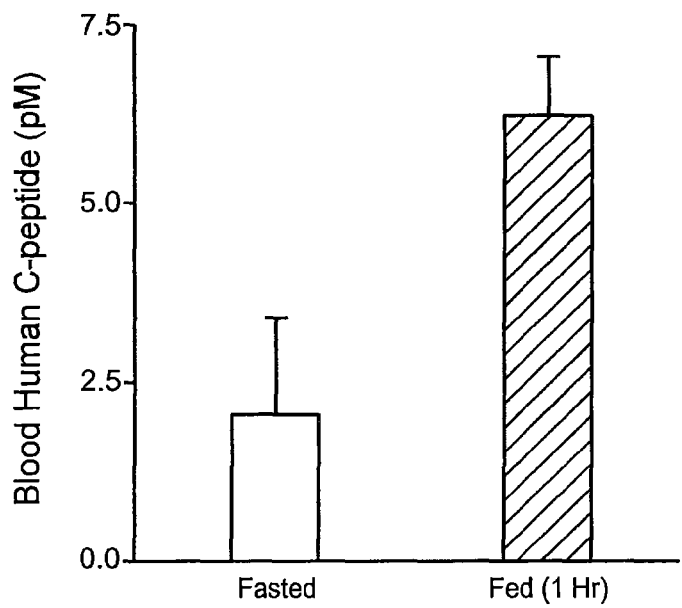
Figure 11:
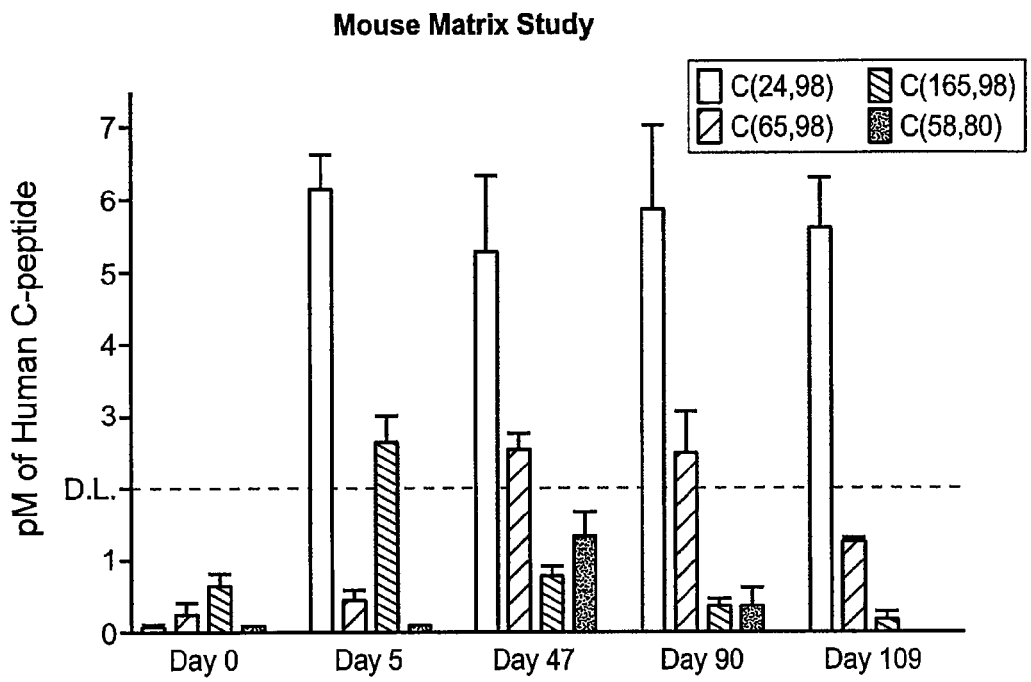
FIG. 11 shows results of a matrix study analyzing the production of human C-peptide over time in mice treated with different chitosan-based nanoparticles carrying GIP-hINS gene.
Figure 12:
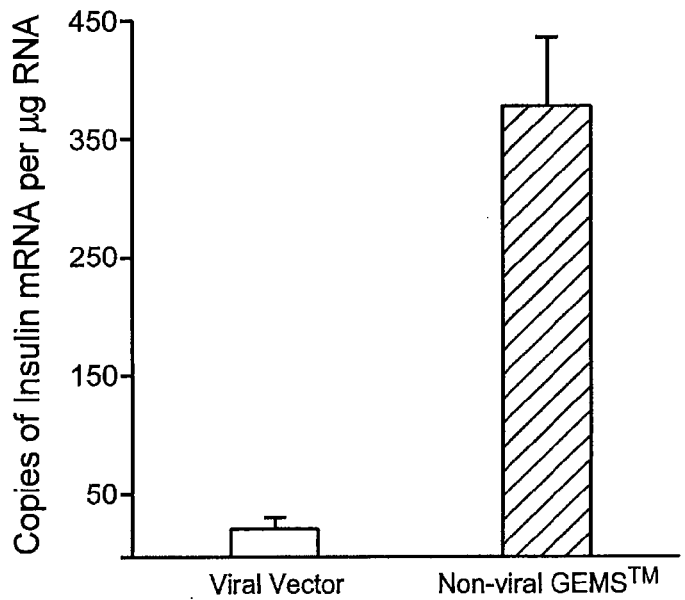
FIG. 12 shows results of human insulin mRNA measurement in duodenum of pigs treated with chitosan-based nanoparticles carrying hGIP-hINS gene at 7 days post delivery.
Figure 13:
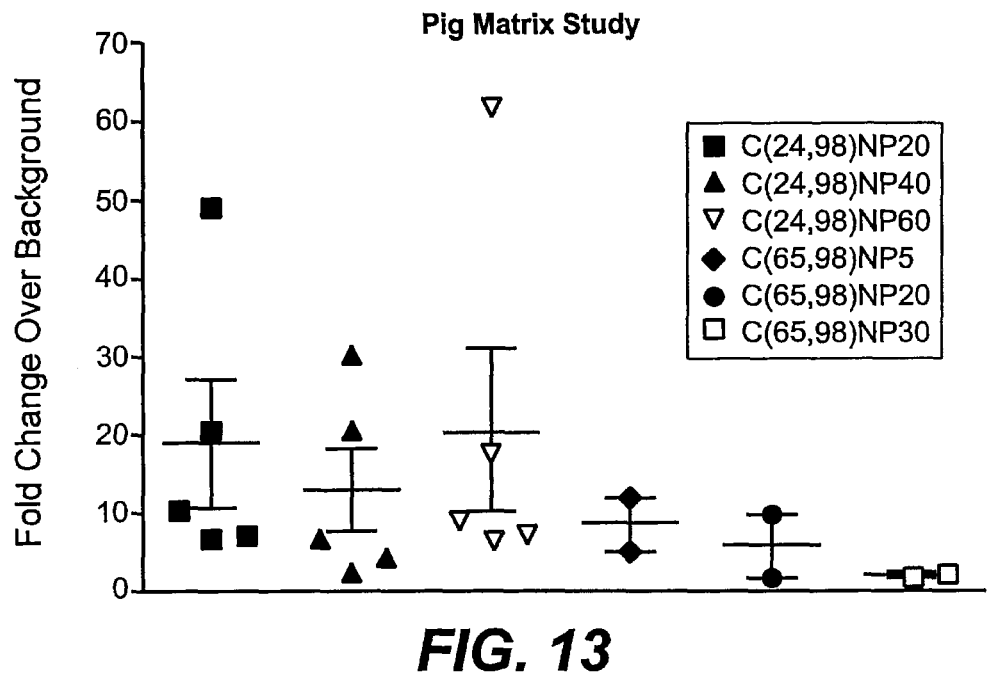
FIG. 13 shows results of a matrix study analyzing the production of human insulin in pigs treated with different chitosan-based nanoparticles carrying hGIP-hINS gene.

To confirm the efficiency of gene transfer using chitosan-based nanoparticles, we delivered naked DNA (pShuttle-CMV-LacZ) or pShuttle-CMV-LacZ packaged with C(24,98) to the duodenum of mice. After 2 days, we found that the gene copy numbers for the group that received chitosan-DNA nanoparticles was more than 100-fold higher than the group that received naked DNA (FIG. 8, left). This confirms the ability of chitosan-based nanoparticles to effectively deliver DNA to the cells of the duodenum.

A plasmid containing an expression cassette of a luciferase marker gene and attB sequence (pLuc-attB) was packaged with C(24,98) with or without the ΦC31 integrase expression plasmid (pCMV-INT) and delivered to the duodenal lumen of mice. When a ΦC31 integrase expression plasmid was co-packaged in the nanoparticles, the presence of the marker gene persisted in the gut mucosa at 14 days post-delivery at a level that was over 100 fold higher than in mice treated with nanoparticles carrying the pLuc-attB plasmid alone. The significantly higher levels of luciferase gene in the gut at 14 days post vector delivery indicates that the ΦC31 integrase successfully integrated the transgene into a long-living duodenal mucosal precursor cell population.

C-Peptide Levels in Mouse Plasma after Delivery of C(24, 98)-GIP-INS or C(1119, 74)-GIP-INS Polyplex Formation: Plasmid DNA and chitosan solutions, prepared separately, were adjusted to a concentration equal to two-times the required final concentration. For P1 (C(24,98)), DNA was diluted in water and the indicated chitosan was dissolved in 0.5 mM sodium acetate, pH5.0. For RC05 (C(1119,74)), DNA was diluted in 50 mM sodium sulfate solution, and the indicated chitosan was dissolved in 5 mM sodium acetate, pH5.5. In each case, both solutions were incubated at 55° C. for 5 minutes before being mixing. Equal volumes of the two solutions were mixed and rapidly vortexed for 30 seconds to form DNA/chitosan particles. Chitosan used was obtained from FMC (Norway) and Biosyntech (Canada).

Plasma collection: Mouse plasma was collected from the saphenous vein of mice at various time points after luminal delivery of C(24,98)-GIP-INS or C(1119,74)-GIP-INS (total DNA dose=10 μg/animal). The mice were fasted overnight and then given 2 g of glucose per kg of mouse 15 minutes prior to the blood collection. Human C-peptide levels in mouse plasma were determined by using the ALPCO Ultra-Sensitive Insulin ELISA kit following the manufacturer's recommendations, with minor modifications. These modifications included: mouse plasma diluted 1:2 instead of using neat and incubated in the assay buffer for 2 h instead of 1 h.

Results (FIG. 9): To evaluate the potential therapeutic efficacy of nanoparticles in targeting insulin production to gut K-cells, we packaged the GIP/Ins transgene with attB sequence (pmGIP-hINS-WPRE-attB) and ΦC31 integrase expression plasmid (pCMV-INT) (INS:INT ratio=5:1) with chitosan (either C(24,98) NP=60 or C(1119,74) NP=2.9) and delivered the polyplex to the duodenum of mice, using the luminal delivery method described above. We were able to achieve detectable circulating levels of human C-peptide in mice for over 120 days. Following a single vector administration with C(24,98) polyplex to the duodenum, the mean levels of plasma human C-peptide obtained in these mice reached as high as 10 pM after about 80 days following vector delivery. In contrast, animals that received C(1119,74)-GIP-INS had an initial early increase in circulating C-peptide levels, followed by sustained low levels and loss of C-peptide by 100 days. This study shows that low molecular weight chitosan nanoparticles are more effective at achieving robust insulin production and secretion by K cells for periods longer than 50 days.

(FIG. 10) To determine if in vivo human insulin production and secretion from K-cells is meal-regulated, overnight fasted mice were given 0.5 g standard chow pellet that was consumed entirely in ~8 minutes or 2 g/kg body weight of dextrose via oral gavage. Thirty minutes after the introduction of food or fifteen minutes after introduction of dextrose, plasma human C-peptide in treated animals increased significantly, from >2 pM fasted level to ~4.8-6 pM post introduction of dextrose or standard chow. 60 minutes post oral gavage of dextrose solution, the human C-peptide level return to basal level. These results indicate that insulin secretion from gut K-cells is meal-regulated; and like b-cells, they are capable of secreting insulin rapidly in response to a meal.

C-Peptide Levels in Mouse Plasma after Delivery of Various Chitosan-GIP-Ins Particles Polyplex Formation (data FIGS. 11-14): Chitosan powder was added to 0.5% aqueous solution of acetic acid until the chitosan working solution reaches pH 4.8. The working solution is then filtered through a membrane filter (Acrodisc 0.2 μm pore size, Pall Life Sciences). Stock DNA solutions (in 1×TE) of plasmid A and plasmid B were mixed in a 5:1 ratio of plasmid A to plasmid B, diluted in water, and then filtered through a membrane filter (Acrodisc 0.2 μm pore size, Pall Life Sciences) to produce the DNA working solution. The concentrations of the working solutions were varied in order to produce a final product with the desired DNA and chitosan concentrations according to Table 6. DNA-Chitosan polyplexes were manufactured by continuous in-line mixing of chitosan and DNA working solutions at a volume ratio of 2:1.

TABLE 6

Required working solution concentrations for different polyplex formulations

| Chitosan mer and DDA | Target NP Ratio | Concentration in Mixed Polyplex | | Concentration in Working Solutions | |
| --- | --- | --- | --- | --- | --- |
| | | DNA (mg/mL) | Chitosan (mg/mL) | DNA (mg/mL) | Chitosan (mg/mL) |
| C(24, 98) | 20 | 0.075 | 0.75 | 0.1125 | 2.25 |
| C(24, 98) | 40 | 0.075 | 1.5 | 0.1125 | 4.5 |
| C(24, 98) | 60 | 0.075 | 2.25 | 0.1125 | 6.75 |
| C(65, 98) | 5 | 0.075 | 0.1875 | 0.1125 | 0.5625 |
| C(65, 98) | 20 | 0.075 | 0.75 | 0.1125 | 2.25 |
| C(65, 98) | 30 | 0.075 | 1.125 | 0.1125 | 3.375 |
| C(24, 98) | 20 | 0.25 | 2.5 | 0.375 | 7.5 |
| C(65, 98) | 5 | 0.25 | 0.625 | 0.375 | 1.875 |
| C(165, 98) | 2 | 0.25 | 0.25 | 0.375 | 0.75 |
| C(58, 80) | 5 | 0.25 | 0.802 | 0.375 | 2.406 |

Polyplex delivery to mice was done as described above.

Mouse plasma collection: Mouse plasma was collected from the saphenous vein of mice at various time points after luminal delivery of C(24,98)-GIP-INS, C(65,98), C(165,98) or C(58,80) (total DNA dose=50 μg/animal).). The mice were fasted overnight and then given 2 g of glucose per kg of mouse 15 minutes prior to the blood collection. Human C-peptide levels the mouse plasma were determined by using the ALPCO Ultra-Sensitive Insulin ELISA kit following the manufacturer's recommendations, with minor modifications. These modifications included: mouse plasma diluted 1:2 instead of using neat and incubated in the assay buffer for 2 h instead of 1 h.

Results (FIG. 11): We performed a study to compare the efficiency of targeted insulin production in the K cells of the mice with various chitosan polymers varying in chain length and percentage deacetylation (DDA). Chiosan polyplex were formulated to contain the human insulin gene linked to the rat GIP promoter (pmGIKP-hINS-WPRE-attB) and the a ΦC31 integrase expression plasmid (pCMV-INT) (INS:INT ratio=5:1). We found that C(24,98) resulted in the highest levels of human C-peptide production starting 5 days after administration and that these levels were sustained throughout the study duration of 109 days. Longer chain polymers with the same DDA, C(65,98) and C(165,98), initially produced significant but lower levels of human C-peptide, which declined to below the detection limit by 50 days. Use of nanoparticles comprised of intermediate length polymers having a lower degree of deacetylation (DDA) did not result in significant human C-peptide levels at the given N:P ratio and DNA concentration. This study shows that low molecular weight chitosan nanoparticles are more effective at achieving robust insulin production and secretion by K cells for periods longer than 50 days. Further, this study and the results shown above in FIG. 9 support that in addition to providing for a longer duration of expression, low molecular weight chitosan nanoparticles provide for higher levels of expression. Without being bound by theory, this appears to reflect the ability of low molecular weight chitosan nanoparticles to transfect greater numbers of precursor cells, resulting in a greater numbers of descendant cells (including K cells) having an integrated GIP-insulin transgene.

Human GIP Promoter-Driven Expression of Human Insulin in Pig Duodenum

Chitosan/DNA polyplex preparation was done as described above (FIG. 11). The FIV vector plasmid carrying the rat GIP promoter linked to human insulin transgene (FIV-rGIP/hIns) was generated with the well-established three-plasmid transfection system. To package the rGIP/hIns transgene into VSV-G pseudotyped FIV viral particles, 293T cells are transfected with vector plasmids pFLX-rGIP/hIns, packaging plasmid (pCPRΔEnv) and pCMV-VSV-G for pseudotyping. In detail, 293T cells are passed into thirty 150 mm tissue culture dishes the day before transfection. A total of 20 ug of DNA (8 ug of pFLX-rGIP/hIns, 8 ug of pCPRΔEnv and 4 ug of pCMV-VSV-G) are transfected into 80% confluent cells using calcium phosphate precipitation method. Eight hours after transfection, cells are fed with fresh Dulbecco's Modified Eagle Media (D-MEM) containing 10% FCS and incubated at 37° C. overnight. The culture media is replaced the next morning and the transfected cells are transferred to a 32° C. incubator. Viral particles are harvested from the culture media at 48 h and 72 h post transfection. The supernatant containing the viral particles is clarified by low speed centrifugation, filtered through 0.45 mm filters and subsequently concentrated by centrifugation at 38,000 g for 2.5 h at 4° C. The pellet is then re-suspended in THE buffer (50 mM of Tris and 130 mM of NaCl and 1 mM of EDTA). Concentrated FIV vector is stored at −80° C. For each batch of viral vector produced, vector titers are determined by real-time PCR using probes specific for the human insulin.

Yorkshire and Yucatan pigs were obtained through the University of British Columbia Animal Care Centre (ACC) under enGene's UBC Protocol A03-0101 (Gene Transfer to Intestinal Cells of Mammals). Study protocols were reviewed and approved independently by the Animal Care and Biohazard Committees at UBC. Animals were housed at the ACC and transported to the Animal Resource Centre (ARU) where endoscopic procedures and tissue collection were performed.

Pigs were fasted overnight and pre-medicated by intramuscular injection of a mixture of atropine (0.04-1.00 mg/kg), ketamine hydrochloride (10-20 mg/kg), and rompun (0.1 mg/kg) by ARU staff. Subsequently, endotracheal intubation was performed on the animal for the delivery of 2% isoflurane, which was maintained throughout the entire procedure. Ringer's lactate was administered by intravenous catheterization for volume replacement. Pigs weighed between 29 and 51 kg at the time of vector delivery.

Pigs were placed in a dorsal recumbency with the abdominal region cleaned with hibi-cleanse, sanitized with alcohol and sterilized with iodine. A midline incision was made using cautery through the skin from the level of the zyphoid process moving distal to the inguinal region. The same incision was repeated through the underlying muscle layers and the linea alba using a 10 blade scalpel. Four laparotomy towels were placed along the midline to allow for placement of an abdominal retractor. The pyloric sphincter and proximal duodenum were isolated and six sections were marked off with superficial circular suture patterns using 4.0 vicryl. Superficial injections (2.5 ml per injection site) were made into the mucosa within the marked off treatment site.

Seven days after delivery, pigs were pre-medicated and anesthetized as described above. The abdomen was surgically opened as described above to locate the marked region of the duodenum. Clamps were placed proximal and distal to the treatment site to clamp off the duodenum. Blood vessels adjacent to the duodenum were clamped and then severed. The clamped duodenal sections were incised and the segment removed from the abdomen and placed into ice-cold saline for washing. Following clamp removal, the duodenum was cut open longitudinally, washed with fresh ice-cold saline and pinned to a cutting board. A scalpel was used to dissect the marked regions of duodenum with a 5 mm outer margin to ensure all treated tissue is harvested. Each of these sections was then cut into 2 for both RT-Q-PCR and IHC. Tissue samples for RT-qPCR were submerged in TRIzol reagent (Invitrogen Canada Inc; Burlington, ON), then snap-frozen in dry ice. Tissue samples for IHC were harvested and fixed in the 4% parafomaldehyde.

Real-time quantitative RT-PCR(RT-q-PCR): Tissues in TRIzol reagent was homogenized using a ultra-turrax T8 homogenizer (IKA Works Inc.; Wilmington, N.C.). Total tissue RNA was isolated and purified according to the manufacture's protocol.

Each RNA sample was first digested by DNase I (Invitrogen) to remove any DNA contamination. To each 1 ug sample of RNA, 1 µL 10× DNase I Reaction Buffer, 1 µL DNase I and RNase/DNase free water were added to a final volume of 10 µL. The tubes were incubated for 15 minutes at RT and then the DNase I was inactivated by addition of 1 µL of 25 mM EDTA. The samples were heated for 10 minutes at 65° C.

Reverse Transcription: First-Strand cDNA was synthesized by using SuperScript™ II Reverse Transcriptase (Invitrogen). Following DNA digestion, 1 µL each of Random Primer (Invitrogen) and 10 mM dNTP mix (Invitrogen) were added to each tube, which was heated 65° C. for 5 minutes, then put on ice. To each tube, the following were added: 4 µL of 5× first-Strand Buffer (Invitrogen), 2 µL of 0.1M DTT, and 1 µL of RNaseOUT™ Recombinant Ribonuclease Inhibitor (Invitrogen), and the tubes were incubated at 42° C. for 2 minutes. 1 µL of SuperScript™ II was then added and the tubes were incubated at 42° C. for 50 minutes. Finally, the reaction was terminated by heating at 70° C. for 15 minutes.

Real-Time PCR: A pair of PCR primers and a probe were designed to amplify a portion of the human insulin gene and 18S primers were used to normalize the cDNA quantity of 18S and human insulin between tissues from the experimental and control groups. The sequences of the human insulin primers: 5' CGCCCTTGCTGCATCAG 3' (Forward), 5' GCAGGAGGCGCATCCA 3' (Reverse) (IDT Inc.; Coralville, Iowa). The insulin probe used was 6FAM CTCACAC-CTGGTGGAAG MGBNFQ (Applied Biosystems, Foster City, Calif.). 18S primer and probe, TaqMan Master Mix was also purchased from Applied Biosystems. All samples were tested for both insulin gene and 18S. Working in a lamina flow hood, duplicate samples were loaded into a MicroAmp® optical 96-well reaction plate (Applied Biosystems). A 10 µL sample of cDNA (contained 0.3 ug of original RNA), 0.25 uL of probe, 12.5 µL TaqMan Master Mix, 1.125 µL of each insulin primer or 10 uL of sample cDNA (contained 0.5 ng of original RNA), 1.25 uL of 18S primer and probe and 1.25 µL RNase/DNase free water, and 12.5 uL of TaqMan Master Mix were added to each well. All samples were run in a ABI PRISM 7000 Sequence Detection System (Applied Biosystems). The data were normalized by the 18S and the relative quantitative difference between experimental group and control animals was expressed by the Log 2 Fold Change.

Immunohistochemistry (data not shown): Pig duodenum samples were fixed in 4% parafolmaldehyde in 0.1 mol/liter PBC (pH 7.5) for 4 h and washed in 70% ethanol. Paraffin-embedded sections (5 um) were incubated in 10 mM sodium citrate (pH 6.0) solution for 20 min at 95-100° C. and then blocked with 10% normal goat serum (Vector Laboratories, Burlingame, Calif.). The sections were then incubated with rabbit antiserum to human GIP (Cedarlane Laboratories, Ontario, Canada) at a 1:200 dilution or guinea pig anti-swine insulin (DakoCytomation, Carpinteria, Calif.) at a 1:100 dilution for 1 h at room temperature. After washing sections were incubated for 1 h with either goat anti-rabbit Alexa 488 or goat anti-guinea pig Alexa 555 (Molecular Probes, Eugene, Oreg.) at a 1:600 dilution to detect the presence of either insulin or GIP respectively. Finally, the slides were mounted by Vectashield Mounting Medium with DAPI (Vector Laboratories) and viewed using a Leica DMIRB microscope (Leica Microsystems, Richmond Hill, Ontario) equipped with a Photometrics CoolSNAP camera (Roper Scientific, Tucson, Ariz.) and MetaMorph 7.0 imaging software (PerkinElmer LAS Canada, Woodbridge, Ontario).

Results: The human GIP promoter was used to target human insulin expression to K-cells in pre-clinical studies using pigs. The human GIP promoter-linked human insulin cDNA expression cassette with attB sequence and ΦC31 integrase expression plasmid (pCMV-INT) were packaged with small molecular weight chitosan C(24,98) (NP=40, DNA concentration=75 ug/ml) and delivered by injection into a demarcated region in the pig duodenum. Furthermore, the human GIP promoter-linked human insulin cDNA expression cassette was also packaged in a VSVG-pseudotyped FIV vector and delivered by injection in order to compare the gene transfer efficiency between the two vectors. Seven days after vector administration, biopsies from the demarcated area were obtained for quantitative RT-PCR with a human insulin specific primer and probe set and immunostaining with antibodies specific for human insulin and GIP.

(FIG. 12) Quantitative RT-PCR analysis of biopsy samples from both chitosan/DNA polyplex treated and VSV-G pseudotyped FIV vector treated pig duodenum provided detectable human insulin mRNA. This data shows that the human GIP promotor is active in the pig duodenum. Furthermore, human insulin mRNA levels appeared to be almost 10 fold higher in the chitosan/DNA polyplex treated pig when compared to the FIV treated pig demonstrating the ability of chitosan/DNA polyplex to act as an efficient gene delivery vector to the pig duodenum.

Distinct cells immunoreactive for human insulin were detected in mucosal cells of the duodenum. These immunopositive cells exhibit a 'flask-like' shape, which resemble the classical feature of enteroendocrine cells. In addition, double immunofluorescence examination revealed co-localization of insulin with GIP in duodenal cells suggesting that the human GIP promoter used in our vector correctly targets insulin expression to K-cells in pigs (data not shown).

Luminal Delivery in Pig with Different Pre-Wash Conditions

Chitosan/DNA polyplexes were prepared as described above.

Care of Yorkshire and Yucutan pigs is described above.

Pigs were fasted overnight and pre-medicated by intramuscular injection of a mixture of atropine (0.04-1.00 mg/kg), ketamine hydrochloride (10-20 mg/kg), and rompun (0.1 mg/kg) by ARU staff. Subsequently, endotracheal intubation was performed on the animal for the delivery of 2% isoflurane, which was maintained throughout the entire procedure. Ringers lactate was administered by intravenous catheterization for volume replacement. Pigs weighed between 29 and 51 kg at the time of vector delivery.

A fiber-optic endoscope (Olympus, model CF-1T10L) attached to a video camera system (Visera OTV-S7V) was used to access the duodenum. The endoscope contains a working channel through which the biopsy tool, clipping device and catheters were placed. Biopsies were collected in dry ice and later transferred to −80° C. Three haemoclips were placed using the Rotatable Clip Fixing Device (Olympus) to mark the target region for virus delivery. Buscopan (0.3 mg/kg IV) was administered to suppress peristalsis via the IV injection port in the catheter line. One dose was given at the start of the wash procedure and a second dose was administered just prior to delivery of the viral vector solution.

Pre-treatment of duodenum: For all animals the duodenum was treated with 40 ml of either 5% N-acetylycysteine (NAC, pH 7.0) for 10 minutes to remove the mucin layer, 19 mM Sodium acetate pH 5 to adjust the pH of the surrounding environment, a combination of NAC and Sodium acetate, or saline alone. All pre-treatment solutions were delivered with the Hobbs Mistifier spray catheter (REF 2190).

Vector Administration: After the endoscope entered the duodenum, the treatment site (~5 cm) was marked using duodenal clips (Olympus Canada, HX-600-090L) were placed via the open channel of the endoscope. The pre-treatment solutions were then sprayed via a radial spray catheter throughout the entire treatment site. Following pre-treatment, 20 ml of Chitosan/DNA polyplex (DNA concentration=75 ug/ml) containing both pCMV-SEAP-3×FLAG and pCMV-INT plasmids (5:1 volume ratio) were delivered to the treatment site with a Mystifier catheter (REF 2190).

Tissue collection: Seven days after delivery, pigs were pre-medicated and anesthetized as described above. The abdomen was surgically opened as described above to locate the pylorus and proximal region of the duodenum. Clamps were placed across the pyloric sphincter and 25 cm distal to the pylorus to clamp off the duodenum. Blood vessels adjacent to the duodenum were clamped and then severed. The clamped duodenal sections were incised and the segment removed from the abdomen and placed into ice-cold saline for washing. Following clamp removal, the duodenum was cut open longitudinally, washed with fresh ice-cold saline and pinned to a cutting board. A scalpel was used to dissect the proximal and distal regions to remove a marked 2.5 mm outer margin to ensure all treated tissue is harvested. The resultant tissue segment was sectioned into 2.8 cm sections. Each of these sections was then cut into 2 for both RT-Q-PCR and IHC. Tissue samples for RT-qPCR were submerged in TRIzol reagent (Invitrogen Canada Inc; Burlington, ON), then snap-frozen in dry ice. Tissue samples for IHC were harvested and fixed in the 4% parafolmaldehyde.

Real-time quantitative RT-PCR(RT-q-PCR): Tissue in TRIzol reagent were homogenized using a ultra-turrax T8 homogenizer (IKA Works Inc.; Wilmington, N.C.). Total tissue RNA was isolated and purified according to the manufacture's protocol.

Each RNA sample was first digested by DNase I (Invitrogen) to remove any DNA contamination. To each 1 ug sample of RNA, 1 µL 10× DNase I Reaction Buffer, 1 µL DNase I and RNase/DNase free water were added to a final volume of 10 µL. The tubes were incubated for 15 minutes at room temperature and then the DNase I was inactivated by addition of 1 µL of 25 mM EDTA. The samples were heated for 10 minutes at 65° C.

Reverse Transcription: First-Strand cDNA was synthesized by using SuperScript™ II Reverse Transcriptase (Invitrogen). Following DNA digestion, 1 µL each of Random Primer (Invitrogen) and 10 mM dNTP mix (Invitrogen) were added to each tube, which was heated 65° C. for 5 minutes, then put on ice. To each tube, the following were added: 4 µL of 5× first-Strand Buffer (Invitrogen), 2 µL of 0.1M DTT, and 1 µL of RNaseOUT™ Recombinant Ribonuclease Inhibitor (Invitrogen), and the tubes were incubated at 42° C. for 2 minutes. 1 µL of SuperScript™ II was then added and the tubes were incubated at 42° C. for 50 minutes. Finally, the reaction was terminated by heating at 70° C. for 15 minutes.

Real-Time PCR: Pair of PCR primers and a probe were designed to amplify a portion of the marker gene SEAP and 18S primers were used to normalize the cDNA quantity of 18S and SEAP between tissues from the experimental and control groups. The sequences of the SEAP primers were 5'-ACATGTGCCAGACAGTGGAGC-3' (Forward) and 5'-TCTGGAAGTTGCCCTTGACC-3' (Reverse) (IDT Inc.; Coralville, Iowa). The SEAP probe was 6FAMCAG CCACGGCCTACCTGTGCG MGBNFQ (Applied Biosystems; Foster City, Calif.). 18S primer and probe, TaqMan Master Mix were also purchased from Applied Biosystems. All samples were tested for both SEAP gene and 18S. Working in a lamina flow hood, duplicate samples were loaded into a MicroAmp® optical 96-well reaction plate (Applied Biosystems). A 10 µL sample of cDNA (contained 0.3 ug of original RNA), 0.25 uL of probe, 12.5 µL TaqMan Master Mix, 1.125 µL of each SEAP primer or 10 uL of sample cDNA (contained 0.5 ng of original RNA), 1.25 uL of 18S primer and probe and 1.25 µL RNase/DNase free water, and 12.5 uL of TaqMan Master Mix were added to each well. All samples were run in an ABI PRISM 7000 Sequence Detection System (Applied Biosystems). The data were normalized by the 18S and the Log 2 Fold Change expressed the relative quantitative difference between experimental group and the control animals.

Results (data not shown): This study was carried out to identify an effective method for delivering gene vectors to the pig duodenum. Four pre-wash conditions were used including 5% N-acetylcysteine (NAC), 19 mM Sodium Acetate (NaOAc) buffer pH5.0, both 5% NAC and 10 mM NaOAc and saline alone prior to chitosan/DNA polyplex administration. The RT-q-PCR result from pigs exposed to various pre-washing condition demonstrated that 5% NAC pre-washing as well as combination of 5% NAC and 19 mM NaOAc pH5 buffer produced most efficient gene transfer. Since there is no significant statistical difference between the above two pre-washing condition, we concluded that 5% NAC pre-washing alone is sufficient in facilitating chitosan/DNA polypex to transduce pig duodenum. Pre-wash with saline alone gave a negative result demonstrating that saline wash did not enhance gene transduction in the duodenum.

Pig Matrix Study Demonstrates Low Molecular Weight Chitosan Nanoparticles More Robust in Gene Delivery Chitosan/DNA polyplexes were prepared as described above.

Care of Yorkshire and Yucutan pigs is described above.

Manipulation of pigs is described above under the heading Human GIP promoter-driven expression of human insulin in pig duodenum. NAC pre-wash, as described above, was used for all of the experiments to aid in gene transduction.

Results (FIG. 13): DNA-chitosan polyplexes C(24,98) at NP20, 40, 60 and C(65,98) at NP5, 20, 30 were delivered to the duodenal cells to test which polyplexes provide the greatest gene transduction. The RT-q-PCR result from pigs exposed to various DNA-chitosan polyplexes showed that the 24mer produced the greatest gene transfer, and there was no statistically significant difference between the various N:P ratios tested in 24mer preparations. The 65mer was also capable of gene transfer to a lesser extent. We can conclude that C(24,98) provides the most efficient gene transfer.

Oral Delivery of Chitosan/DNA Polyplex to Mouse Stomach and Duodenum

This experiment was conducted to investigate whether chitosan-packaged plasmid DNA delivered orally to mice could lead to gene transfer to and gene expression in mucosal cells of the stomach. A plasmid carrying the GIP promoter-linked human insulin gene construct or a E1Fa promoter linked SEAP gene was mixed with a chitosan (MW: 3.9 kD, Degree of deacetylation=98%) at a N:P ratio of 40:1. The polyplex was packaged and characterized as described above.

Overnight fasted mice were fed 0.5 mL of a suspension containing chitosan-packaged DNA polyplex (at [DNA]=75 µg/ml) in a single bolus via a feeding tube. Four hours after vector delivery, treated animals were returned to their cages with free access to food and water. Two days after oral feeding of the polyplex, animals were sacrificed and their stomach mucosa were collected by tissue scraping. The levels of insulin or SEAP mRNA were quantified by a standard reverse-transcription real-time quantitative PCR assay.

Figure 14:
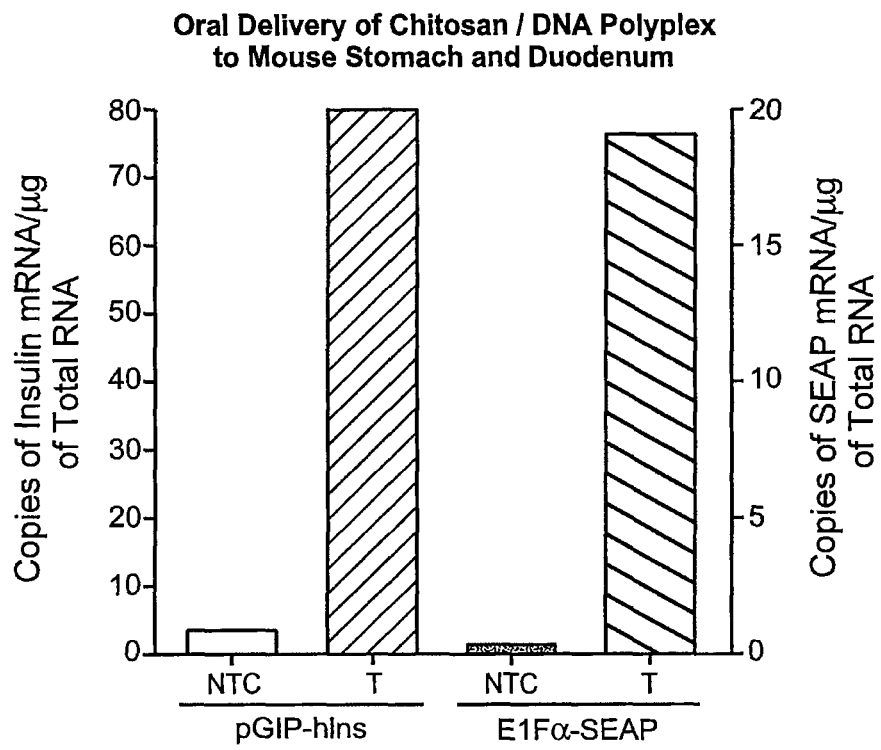
FIG. 14 shows transformation of stomach mucosal cells by oral delivery of a chitosan-packaged DNA polyplex. Levels of insulin and SEAP gene expression levels in the stomach mucosa of mice at 2 days after oral administration of vector. NTC=non-treated controls, T=treated animals.

As show in FIG. 14, simple oral administration of chitosan-packaged DNA particles results in successful transfection and expression of insulin and SEAP gene in stomach mucosa, establishing that transfection of gut mucosal cells in vivo can be achieved by oral administration of a non-viral gene vector.

Physicochemical Characteristics

Particle Sizing

Particle size measurements were made using a Zetasizer Nano light scattering instrument (Malvern Instruments ZEN 3600). In general, samples were undiluted and loaded into a disposable cuvette (Plastibrand 759075D). The Zetasizer was programmed to incubate the sample for 3 minutes at 25° C. prior to triplicate 3-minute measurements. Z-average and polydispersity (PDI) were reported. The Zetasizer was also programmed to account for the composition of the samples with regards to viscosity and refractive index.

Zeta Potential

Zeta potential measurements were made using a Zetasizer Nano light scattering instrument (Malvern Instruments ZEN 3600). In general, samples were undiluted or diluted 5 or 10 fold in 10 mM NaCl and loaded into a Zetasizer folded capillary cell (Malvern Instruments DTS 1060). The Zetasizer was programmed to incubate the sample for 3 minutes at 25° C. prior to measurement. The Zetasizer was programmed to account for the final composition of the samples with regards to viscosity and dielectric constant.

We claim:

1. A method for expressing a therapeutic nucleic acid in a gut mucosal cell, comprising administering a chitosan-based nanoparticle orally, rectally or directly to a gut mucosa; wherein said chitosan-based nanoparticle comprises: (i) a plurality of chitosan polymers having an average molecular weight between 3 kilodaltons (kDa) and 50 kDa; and (ii) a therapeutic construct encapsulated within said plurality of chitosan polymers; wherein said chitosan-based nanoparticle is stable in an agarose gel retention assay; and wherein said therapeutic construct comprises a therapeutic nucleic acid encoding a therapeutic protein operably linked to an expression control region that is functional in a gut mucosal cell.

2. The method according to claim 1, wherein said expression control region comprises a gut-specific promoter.

3. The method according to claim 2, wherein said promoter exhibits constitutive activity.

4. The method according to claim 1, wherein said chitosan-based nanoparticle is capable of effecting expression of said therapeutic nucleic acid in gut mucosa for longer than 4 days.

5. The method according to claim 1, wherein said plurality of chitosan polymers has an average molecular weight less than 25 kDa.

6. The method according to claim 1, wherein said chitosan-based nanoparticle has an amine:phosphate (N:P) ratio between 10:1 and 50:1.

7. The method according to claim 1, wherein said chitosan-based nanoparticle has a diameter less than 225 nm.

8. The method according to claim 1, wherein said plurality of chitosan polymers has an average molecular weight between 3 kDa and 10 kDa.

9. The method according to claim 1, wherein said therapeutic protein is an inhibitor of inflammation.

10. The method according to claim 9, wherein said therapeutic protein is IL-10.

11. The method according to claim 1, wherein said chitosan-based nanoparticles are conjugated with ligands or targeting moieties to enhance specificity or uptake.

12. The method according to claim 1, wherein said chitosan is a chitosan derivative.

13. The method according to claim 1, wherein said chitosan-based nanoparticle is administered endoscopically.

* * * * *